United States Patent
Katsuki et al.

(10) Patent No.: US 6,713,435 B2
(45) Date of Patent: Mar. 30, 2004

(54) METHOD FOR PRODUCING OPTICALLY ACTIVE LACTONE COMPOUNDS BY USING SALEN COBALT COMPLEXES HAVING A CIS-β STRUCTURE

(75) Inventors: Tsutomu Katsuki, Fukuoka (JP); Tatsuya Uchida, Fukuoka (JP); Katsuji Ito, Munakata (JP)

(73) Assignee: Kyushu University, Fukuoka (JP)

(*) Notice: Subject to any disclaimer, the term of this patent is extended or adjusted under 35 U.S.C. 154(b) by 0 days.

(21) Appl. No.: 10/232,517

(22) Filed: Sep. 3, 2002

(65) Prior Publication Data

US 2003/0120091 A1 Jun. 26, 2003

(30) Foreign Application Priority Data

Sep. 3, 2001 (JP) .................. 2001-266047
Jun. 18, 2002 (JP) .................. 2002-176724

(51) Int. Cl.$^7$ .................. A01N 43/40; C07D 305/14; C07D 307/77
(52) U.S. Cl. .................. 504/260; 549/265; 549/299
(58) Field of Search .................. 504/260; 549/295, 549/299

(56) References Cited

U.S. PATENT DOCUMENTS

| | | | | |
|---|---|---|---|---|
| 5,663,393 A | * | 9/1997 | Jacobsen et al. | 556/45 |
| 6,008,190 A | * | 12/1999 | Meade et al. | 514/6 |
| 6,297,389 B1 | * | 10/2001 | Castiglioni et al. | 549/295 |
| 6,323,347 B2 | * | 11/2001 | Chen et al. | 549/295 |
| 6,346,629 B1 | * | 2/2002 | Brunner et al. | 549/295 |
| 6,512,127 B2 | * | 1/2003 | Rossen et al. | 549/323 |
| 6,521,763 B1 | * | 2/2003 | Fischer et al. | 549/295 |
| 6,531,616 B2 | * | 3/2003 | Puts et al. | 549/266 |
| 6,559,322 B1 | * | 5/2003 | Mandal et al. | 549/263 |

FOREIGN PATENT DOCUMENTS

| | | |
|---|---|---|
| DE | 197 45 442 A1 | 4/1999 |
| DE | 198 35 533 A1 | 2/2000 |
| DE | 198 43 875 A1 | 3/2000 |
| JP | 63-122644 A | 5/1988 |

OTHER PUBLICATIONS

Bolm, Carsten et al., "Copper– and vanadium–catalyzed asymmetric oxidations", Journal of Molecular Catalysis A: Chemical 1997, pp 347–350, vol. 117, Elsevier Science B.V. (XP–002238406).

Copper, Mark S. et al., "Oxidation Reactions Using Urea–Hydrogen Peroxide: A Safe Alternative to Anhydrous Hydrogen Peroxide", Synlett, 1990, pp 533–535 (XP–001147750).

Gusso, Andrea et al., "Platinum–Catalyzed Oxidations with Hydrogen Peroxide: Enantiospecific Baeyer–Villiger Oxidation of Cyclic Ketones", Organometallics, 1994, pp 3442–3451, vol. 13, No. 9, Washington, DC (XP–000923391).

Lopp, Margus et al., "Asymmetric Baeyer–Villiger Oxidation of Cyclobutanones", Tetrahedron Letters, 1996, pp 7583–7586, vol. 37, No. 42, Elsevier Science Ltd., Amsterdam, NL.

Uchida, Tatsuya et al., "Cationic Co(III)(salen)–catalyzed enantioselective Baeyer–Villiger oxidation of 3–arylcyclobutanones using hydrogen peroxide as a terminal oxidant", Tetrahedron Letters, 2001, pp 6911–6914, vol. 42, No. 39, Elsevier Science, Amsterdam, NL.

\* cited by examiner

*Primary Examiner*—Deborah C. Lambkin
(74) *Attorney, Agent, or Firm*—Burns, Doane, Swecker & Mathis, LLP

(57) ABSTRACT

A method for producing an optically active lactone compound by Baeyer-Villiger oxidation of a cyclic ketone compound with at least one kind of oxidants selected from the group consisting of hydrogen peroxide and urine-hydrogen peroxide adduct (UHP) using a cobalt(salen) complex having a cis-β structure expressed by the following formula (I) or (II) as a catalyst.

[Formula (I)]

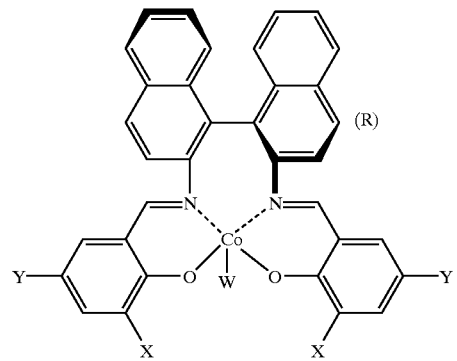

(I)

in which X and Y independently denote H, a t-butyl group or an electron-withdrawing substituting group and W is a halogen element.

[Formula (II)]

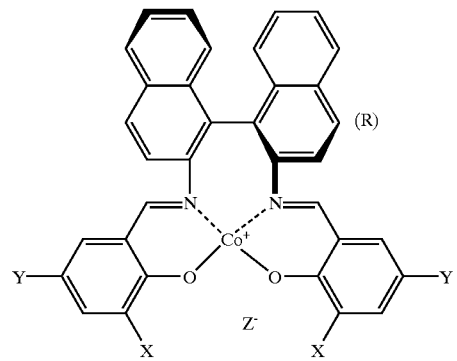

(II)

in which X and Y independently denote H, a t-butyl group or an electron-withdrawing substituting group and Z$^-$ is a monovalent anion. The optically active lactone compounds can be used for the synthesis of medicines and argochemicals.

34 Claims, No Drawings

METHOD FOR PRODUCING OPTICALLY ACTIVE LACTONE COMPOUNDS BY USING SALEN COBALT COMPLEXES HAVING A CIS-β STRUCTURE

BACKGROUND OF THE INVENTION

1. Field of the Invention

The present invention relates to a method for producing optically active lactone compounds. More specifically, the invention relates to a method for producing optically active lactone compounds by Baeyer-Villiger oxidation of cyclic ketone compounds using salen cobalt complexes possessing a cis-β structure as a catalyst. Such optically active lactone compounds can be used for the synthesis of medicines and agrochemicals. Further, both S isomers and R isomers can be synthesized by choosing the catalyst.

2. Related Art Statement

Asymmetric Baeyer-Villiger oxidation is an important reaction in the organic synthetic chemistry. Still, these is no general method for achieving sufficient enantioselectivity in the oxidation. Baeyer-Villiger oxidation starts with nucleophilic attach of an oxidant to a carboxyl group, followed by the migration of the carbonyl-substitutent (R3 or R4) to the vicinal oxygen atom to give a lactone (or esters). Lewis acid accelerates both the nuclceophic addition and the migration through its coordination to the carbonyl group and the leaving group (X'), respectively. The reaction formula is shown below.

[Formula 1]

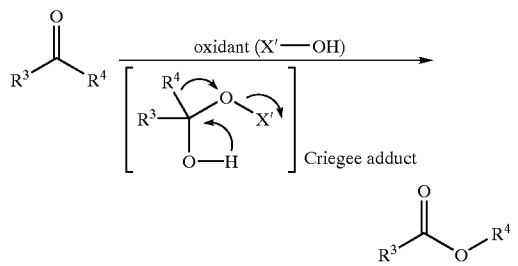

Bolm and co-workers reported enantiomer-differentiating Bayer-Villiger oxidation of racemic 2-substituted cycloalkanones using a combination of molecular oxygen and aldehyde (Mukaiyama condition) in the presence of bis (oxazolinyl-phenolato)copper (II) complex as a catalyst (Bolm C., Schlingloff G. and Weichhardt K., Angew. Chem. Int. Ed. Engl. 1994, 33, 1848–1849). Enantioselective Baeyer-Villiger oxidation using chiral platinum complexes as catalysts were also reported (Gusso A., Baccin C., Pinna F., and Strukul G., Organometallics, 1994, 13, 3442–3451). Thereafter, asymmetric Baeyer-Villiger oxidations using various optically active metal complexes as catalysts have been investigated, and high enatioselectivity has been realized for the reactions of some specific substrates.

However, the maximum enantioselectivity in the reported asymmetric Baeyer-Villiger oxidation of prochiral ketones, particularly, prochiral 3-substituted cyclobutanone compounds by using optically active metal complexes as catalyst was 47%ee (until August, 2001) (Lopp M., Paju A., Kanger T., and Pehk T., Tetrahedron Lett., 1996, 37, 7583–7586, Bolm C., Schlingloff G., and Bienewald E, J. Mol. Cat. A; Chem., 1997, 117, 347–350, Bolm C., and Beckmann O., Chirality, 2000, 12, 523–525, Shinohara T., Fujioka S., and Kotsuki, H., Heterocycles, 2001, 55, 237–241).

SUMMARY OF THE INVENTION

Therefore, it is an object of the present invention to provide a method for producing lactone compounds at an optically high purity by asymmetric Baeyer-Villiger oxidation of prochiral ketones.

Having made strenuous investigations to solve the above-mentioned problems, the inventors discovered that lactone compounds of optically high purities could be produced by the Baeyer-Villiger oxidation of cyclic ketone compounds with specific oxidants in the presence of cobalt(salen) complexes of cis-β structure as catalyst. The present invention was accomplished based on this discovery.

(1) That is, the present invention relates to a method for producing an optically active lactone compound by Baeyer-Villiger oxidation of a cyclic ketone compound with at least one kind of oxidants selected from the group consisting of hydrogen peroxide and urine-hydrogen peroxide adduct (UHP) in the presence of a cobalt(salen) complex possessing cis-β structure expressed by the following formula (I) or (II) as a catalyst.

[Formula (I)]

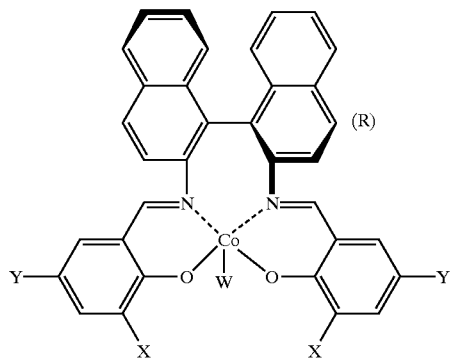

in which X and Y independently denote H, t-butyl group or an electron-withdrawing substituting group and W is a halogen element.

[Formula (II)]

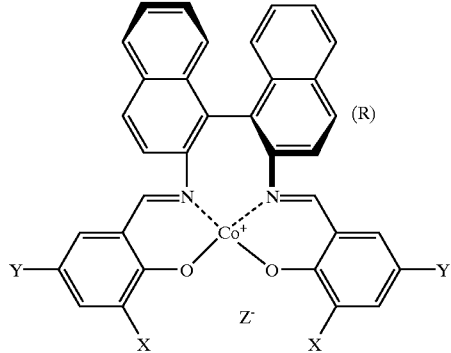

in which X and Y independently denote H, t-butyl group or an electron-withdrawing group and Z⁻ is a monovalent non-coordinating anion.

The followings are preferred embodiments of the lactone-producing method of the present invention.

(2) X and Y in the cobalt(salen) complex of the formula (I) independently denote t-butyl group, F, Cl, Br, I or a nitro group.

(3) X and Y in the cobalt(salen) complex of the formula (I) denote t-butyl group and nitro group, respectively.
(4) W in the cobalt(salen) complex of the formula (I) denotes iodine.
(5) X and Y in the cobalt(salen) complex of the formula (II) independently denote F, Cl, Br or I.
(6) X and Y in the cobalt(salen) complex of the formula (II) denote F.
(7) $Z^-$ in the cobalt(salen) complex of the formula (II) denotes non-coordinating anion such as $SbF_6^-$.
(8) The cyclic ketone compound is represented by any one of the following formulae (III), (IV) and (V).

[Formula (III)]

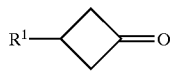

(III)

in which $R^1$ is a substituted or non-substituted C1–C20 alkyl group or a substituted or non-substituted C6–C15 aryl group.

[Formula (IV)]

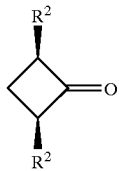

(IV)

in which $R^2$ is a substituted or non-substituted C1–C20 alkyl group or a substituted or non-substituted C6–C15 aryl group.

[Formula (V)]

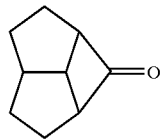

(V)

(9) The cyclic ketone compound is represented by the formula (III).
(10) The cyclic ketone compound is 3-phenylcyclobutanone, 3-(p-chlorophenyl)cyclobutanone, 3-(p-methoxyphenyl)cyclobutanone or 3-octyl cyclobutanone.
(11) The cyclic ketone compound is represented by the formula (V).
(12) The lactone compound is represented by any one of the following formulae (VI), (VII) and (VIII).

[Formula (VI)]

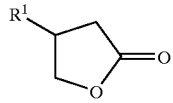

(VI)

in which $R^1$ is a substituted or non-substituted C1–C20 alkyl group or a substituted or on-substituted C6–C15 aryl group.

[Formula (VII)]

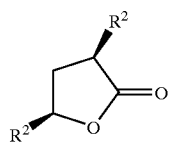

(VII)

in which $R^2$ is a substituted or non-substituted C1–C20 alkyl group or a substituted or non-substituted C6–C15 aryl group.

[Formula (VIII)]

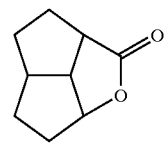

(VIII)

(13) The lactone compound is represented by the formula (VI).
(14) The lactone compound is β-phenyl-γ-butylolactone, β-(p-chlorophenyl)-γ-butylolactone, β-(p-methoxyphenyl)-γ-butylolactone or β-octyl-γ-butylolactone.
(15) The lactone compound is represented by the formula (VIII).
(16) The lactone compound has an optical purity of not less than 47% ee.
(17) The lactone compound-producing method further uses at least one kind of polar solvents.
(18) The polar solvent is any one selected from acetonitrile, ethyl acetate, diethyl ether, tetrahydrofuran (THF) and a C1–C3 alcohol.
(19) The Baeyer-Villiger oxidation is effected in a temperature range of −20° C. to 25° C.

Any combinations of (2) to (19) are also preferred embodiments of the lactone-producing method according to the present invention, so long as no discrepancy occurs.

The present invention also relates to a catalyst to be used in the above-mentioned methods, that is,

(20) the invention relates to a cobalt(salen) complex having a cis-β structure represented by the following formula (I) or (II).

[Formula (I)]

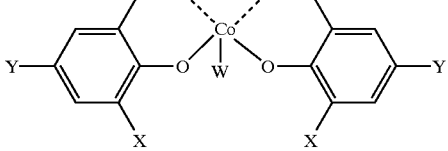

in which in which X and Y independently denote H, t-butyl group or an electron-withdrawing group and W is a halogen element.

[Formula (II)]

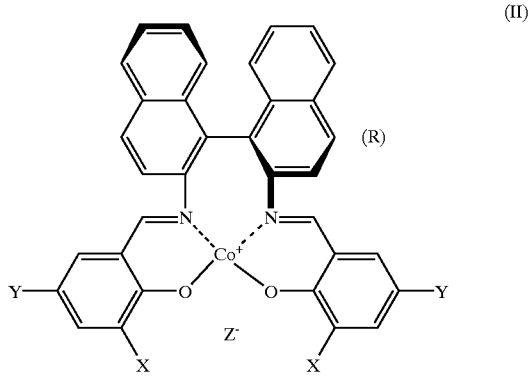

in which X and Y independently denote H, t-butyl group or an electron-withdrawing group and $Z^-$ is a monovalent non-coordinating anion.

The followings are preferred embodiments of the complexes of the present invention.

(21) X and Y in the cobalt(salen) complex of the formula (I) independently denote t-butyl group, F, Cl, Br, I or nitro group.
(22) X and Y in the cobalt(salen) complex of the formula (I) denote t-butyl group and nitro group, respectively.
(23) W in the cobalt(salen) complex of the formula (I) denotes iodine.
(24) X and Y in the cobalt(salen) complex of the formula (II) independently denote F, Cl, Br or I.
(25) X and Y in the cobalt(salen) complex of the formula (II) denote F.
(25) $Z^-$ in the cobalt(salen) complex of the formula (II) denotes non-coordinating anion such as $SbF_6^-$.

Any combinations of (21) to (26) are also preferred embodiments of the catalyst of the present invention, so long as no discrepancy occurs.

These and other objects, features and advantages of the invention will be apparent from reading of the following detailed description of the invention when taken with the understanding that some variations, changes or variations could be easily made by the skilled person in the art to which the invention pertains.

DETAILED DESCRIPTION OF THE INVENTION

In the following, the present invention will be explained in more detail. The Baeyer-Villiger oxidation utilized in the producing method according to the present invention, which is also called the Baeyer-Villiger reaction or the Baeyer-Villigar rearrangement, is a reaction in which an ester is produced by oxidation of a ketone with peroxide. The lactone is obtained by subjecting the cyclic ketone compound to this reaction. Further, the optically active lactone compound is obtained by subjecting the prochiral cyclic ketone compound to the above reaction.

The Baeyer-Villiger oxidation consists of two steps: (i) nucleophilic attack of an oxidant to a carbonyl compound to give Criegee adduct and (ii) rearrangement of the adduct to give an ester (or lactone). Therefore, the stereochemistry of the Baeyer-Villiger oxidation is influenced by two factors: (i) the face-selectivity in the addition of the oxidant and (ii) the enantiotopos-selectivity in the rearrangement. According to the present invention, the Baeyer-Villiger oxidation of the prochiral cyclic ketone compounds with use of the specific metal catalysts and specific oxidants as mentioned later improves the face-selectivity and the enantiotopos-selectivity, so that the optically active lactone compounds are obtained.

The cobalt(salen) complex possessing the cis-β structure to be used as the catalyst in the present invention is expressed by either one of the following formulae (I) and (II).

[Formula (I)]

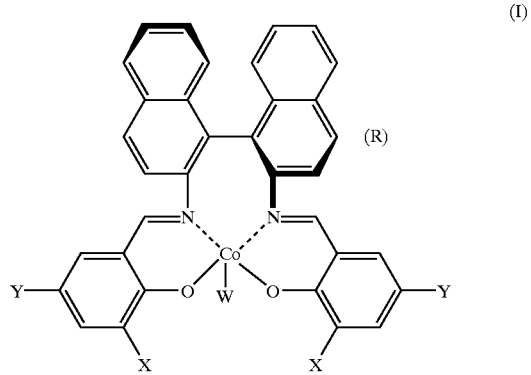

[Formula (II)]

(II)

In the formula (I), X and Y independently denote H, t-butyl group or an electron-withdrawing group. As the electron-withdrawing group, halogen elements such as F, Cl, Br and I as well as a nitro group may be recited. As X and Y in the formula (I), t-butyl group, F, Cl, Br, I and nitro group are preferred. It is particularly preferable that X is t-butyl group and Y is nitro group. W is a halogen element, and Br and I are recited as the halogen element. I is preferred, because I weakly bonds to cobalt and easily dissociates therefrom in the reaction system.

In the formula (II), X and Y independently denote H, t-butyl group or an electron-withdrawing group. As the electron-withdrawing group, the same as referred to in the explanation of X and Y in the formula (I) are recited. As X and Y in the formula (II), F, Cl, Br and I are preferred. It is particularly preferable that both X and Y are F. $Z^-$ is a monovalent non-coordinating anion. For example, $SbF_6^-$ and $PF_6^-$ may be reicted, and $SbF_6^-$ is preferred. Since $Z^-$ is the monovalent non-coordinating anion, the complex represented by the formula (II) is cationic.

The cobalt(salen) complex represented by the formula (II) is obtained by reacting the cobalt(salen) complex of the formula (I) with silver hexafluoroantimonate or the like, for example. Therefore, the cobalt(salen) complex of the formula (I) is more easily synthesized as compared with that of the formula (II). The cobalt(salen) complex of the formula (I) is more easily handled than that of the formula (II). Therefore, the cobalt(salen) complex of the formula (I) is more preferable from the standpoint of the production cost and the handling easiness of the complex.

The loading amount of the catalyst according to the present invention is preferably in a range of 1 to 10 mol %, more preferably 4 to 6 mol % relative to 1 mol of the cyclic ketone as the substrate.

The cationic cobalt(salen) complex of the formula (II) has two vacant coordinating sites adjacent to each other above the central metal, and these coordinating sites are available for coordination of the substrate and the oxidant. On the other hand, in the cobalt(salen) complex of the formula (I), W coordinating to the central metal is easily dissociated in the reaction system, so that the cobalt ion can possess two vacant coordinating sites adjacent to each other, and these coordinating sites are available for the coordination of the substrate and the oxidant.

Therefore, when the cobalt(salen) complex of either the formula (I) or (II) is used for the asymmetric Baeyer-Villiger oxidation, the oxygen atom of the carbonyl group of the substrate and the oxygen atom of the oxidant simultaneously on stepwise coordinate to the central metal and the Baeyer-Villiger oxidation occurs in the coordination sphere of the cobalt ion. Accordingly, the face-selectivity in nucleophilic attack of the oxygen atom of the oxidant to the carbon atom of the carbonyl group of the substrate and enantiotopos-selectivity in the rearrangement of the Criegee adduct resulting from the nucleophilic attack are achieved. Therefore, the cobalt(salen) complex used in the producing method of the present invention is required to have two vacant coordinating sites adjacent to each other above the metal on which the desired Baeyer-Villiger oxidation proceeds.

The cyclic ketone compound to be used in the present invention is a prochiral cyclic ketone compound, which forms a chiral carbon in the Baeyer-Villiger oxidation. For example, the compounds represented by the following formulae (III), (IV) and (V) are recited. In this application, the prochiral cyclic ketone compounds mean the cyclic ketones that form a chiral carbon through the reaction.

[Formula (III)]

(III)

in which $R^1$ is a substituted or non-substituted C1–C20 alkyl group or a substituted or non-substituted C6–C15 aryl group.

[Formula (IV)]

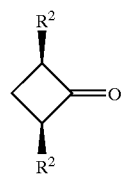

(IV)

in which $R^2$ is a substituted or non-substituted C1–C20 alkyl group or a substituted or non-substituted C6–C15 aryl group.

[Formula (V)]

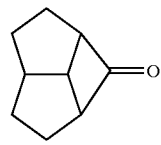

(V)

As the alkyl group in $R^1$ of the formula (III), methyl, ethyl, propyl, isopropyl, butyl, isobutyl, t-butyl, pentyl, isopentyl, neopentyl, hexyl, heptyl, octyl, 2-ethylhexyl, nonyl, decyl, undecyl, dodecyl, tridecyl, isotridecyl, myristyl, palmityl, stearyl, eicocyl, docosyl, etc. may be recited.

As the aryl group in $R^1$ of the formula (III), phenyl, tolyl, xylyl, cumyl, mesityl, ethylphenyl, propylphenyl, butylphenyl, pentylphenyl, hexylphenyl, heptylphenyl, octylphenyl, nonylphenyl, α-naphthyl, β-naphthyl, etc. may be recited.

The above alkyl group and aryl group may be substituted by a halogen, a C1–C4 alkoxy group or the like.

As the alkyl group and the aryl group in $R^2$ of the formula (IV), those recited as the alkyl group and the aryl group in $R^1$ of the above formula (III) may be also recited. These alkyl groups and aryl groups may be substituted by a halogen, a C1–C4 alkoxy group or the like.

The oxidant to be used in the present invention is hydrogen peroxide or an urea-hydrogen peroxide adduct (UHP). Each of these oxidants coordinates to the central metal of the cobalt(salen) complex, attacks the carbonyl group as the substrate and produces the chelated Criegee adduct. Another possibility is that the oxidant attacks the carbonyl compound and coordinates to the central metal to give the chelated Criegee adduct. On the other hand, if t-butyl hydroxyperoxide (TBHP) or metha-chloroperbenzoic acid (m-CPBA) is used as the oxidant, the oxidant attacks the carbonyl compounds to produce a non-chelated Criegee adduct an intermediate. In this case, since the oxygen atom of the carbonyl group as the substrate and the oxygen atom of the oxidant do not simultaneously coordinate to the central metal, the enantioselectivity is extremely deteriorated. The use amount of the above oxidant is preferably 1 to 2 equivalents, more preferably 1.2 to 1.3 equivalent relative to the cyclic ketone as the substrate.

The optically active lactone compound as the product of the present invention is produced by subjecting the above-mentioned prochiral cyclic ketone compound to the asymmetric Baeyer-Villiger oxidation. Since the enantiotopos-selective rearrangement of the chelated Criegee adduct is high in the producing method of the present invention as mentioned above, the optically active lactone compound is obtained. The optically active lactone compounds produced form the cyclic ketones by the present invention have formulae (VI), (VII), (VIII), etc. and are recited.

[Formula (VI)]

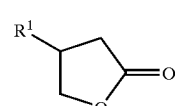

(VI)

in which R¹ has the same meaning as mentioned above.

[Formula (VII)]

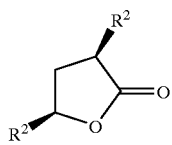
(VII)

in which R² has the same meaning as mentioned above.

[Formula (VIII)]

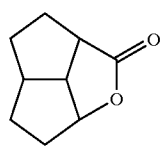
(VIII)

The optical purity to be used as an index for the purity of the optical isomer of the present invention is expressed by the following formula.
[Mathematical formula]

Optical purity (%ee) =

$$\frac{[\alpha]_D \times 100}{[\alpha]_{Dmax}} = \frac{(R-S) \times 100}{R+S} \text{ or } \frac{(S-R) \times 100}{R+S} = \text{Enantiometric excess percentage (\%ee)}$$

in which $[\alpha]_D$ is a specific optical rotation degree of a sample, $[\alpha]_{Dmax}$ is a specific optical rotation degree of an optically pure substance, R is a ratio of an R isomer in the sample, and S is a ratio of an S isomer in the sample. Therefore, the optical purity is equal to the excess ratio of the enantiomers. If the ratio of the R isomer is equal to that of the S isomer, that is, if the sample is a racemic product, the optical purity is 0% ee. The optical purity (excess ratio of the enantiomers) of the product can be measured by a high performance liquid chromatography (HPLC) using an optically active column.

The producing method of the present invention is usually effected in a solvent. As the solvent, halogenated alkanes such as dichloromethane, ether compounds such as tetrahydrofuran (THF) and diethyl ether, nitrile compounds such as acetonitrile, esterified compounds such as ethyl acetate, C1–C3 alcohol compounds such as methanol, ethanol and isopropanol, aliphatic hydrocarbons such as hexane, aromatic hydrocarbons such as benzene and toluene, etc. may be recited. Among them, polar solvents such as the halogenated alkane, the ether compound, the nitrile compound, the ester compound and the alcohol compound are preferred from the standpoint of enhancing the reaction speed and the excess percentage of the enantiomers. Acetonitrile, ethyl acetate, tetrahydrofuran, diethyl ether and the C1–C3 alcohol compounds are particularly preferred. The use amount of the solvent is preferably 1–10 ml, more preferably 4–5 ml relative to 1 mmol of the cyclic ketone as the substrate.

The producing method of the present invention can be effected at room temperature. The reaction is preferably effected at not more than room temperature, for example, 0° C. to −20° C., because the optical purity of the product increases due to the enhanced excess percentage of the enantiomers, although the yield of the product decreases in the reaction at such a temperature.

According to the present invention, the optically active lactone compound can be produced by stirring a mixed solution of the cyclic ketone compound, the oxidant, the solvent and the catalyst. Stirring is not limited to a particular way so long as the uniformity of the mixed solution can be ensured. A known stirring method can be used. The reaction time is not particularly limited, and appropriately selected depending upon the reaction temperature. It is preferable that the higher the reaction temperature, the shorter is the reaction time, whereas the lower the reaction temperature, the longer is the reaction time.

EXAMPLES

In the following, the present invention will be explained in more detail with reference to examples, but the scope of the invention is not limited to these examples.

Complex Synthesis Example 1

Cobalt (II) acetate (tetrahydrate) (manufactured by Kishida Chemical Co., Ltd.) (124.5 mg, 0.5 mmol) was heated at 80° C., and dry in vacuum for one hour. Then, the resultant was returned to room temperature, and dissolved in dehydrated ethanol (5 ml) added in nitrogen flow.

Into ethanol (10 ml) was dissolved (1S,2S)-1,2-diphenylethylene diamine (Kankyou Kagaku Center Co., Ltd.) (106.2 mg, 0.5 mmol). Into the solution was added 3,5-dibromosalicyl aldehyde (Tokyo Kasei Industries, Ltd.) (279.9 mg, 1.0 mmol). The solution was refluxed under heating and stirring for 6 hours. Then, the reaction mixture was returned to room temperature after the completion of the reaction, and the precipitate formed was filtered and dried under heating for one hour. The dried precipitate was added to the above ethanol solution of the cobalt acetate, and the mixture was refluxed under heating for 6 hours. Thereafter, the reaction mixture was returned to room temperature, and the precipitate was filtered in a nitrogen atmosphere, and dried by heating for one hour.

The dried precipitate was dissolved in dichloromethane in nitrogen atmosphere. Iodine (63.5 mg, 0.25 mmol) was added into the solution, which was stirred for one hour. Then, silver hexafluoroantimonate [Aldrich Chem. Co.] (171.8 mg, 0.5 mmol) was added to the resultant, and the mixture was further stirred for one hour. Thereafter, the reaction solution was filtered with Celite, and the filtrate was concentrated with a rotary evaporator, thereby removing dichloromethane. The residue was chromatographed in a silica gel column using dichloromethane/methanol (=20/1) as a developing solvent, thereby obtaining Co (III) (salen) complex having the following formula (IX), that is, [(S,S)-N,N'-bis(3,5-dibromosalicylidene)-1,2-diphenylethylene diaminate cobalt (III)]hexafluoroantimonate (403.0 mg, yield 84%).

[Formula (IX)]

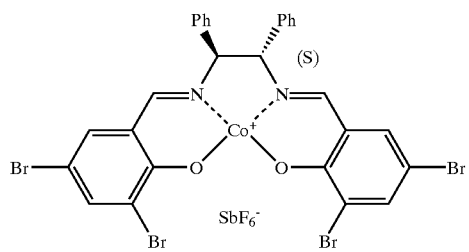

(IX)

Results in IR (KBr) measurement of the complex obtained by the above method were 3065, 3056, 2959, 1632, 1583, 1502, 1439, 1375, 1310, 1217, 1167, 1078, 1005, 964, 864, 789, 748, 714, 664, 550, 521 cm$^{-1}$. An actual measurement result of HRFAB-MS m/z was 788.7429, while the theoretical value of $C_{28}H_{18}O_2N_2{}^{79}Br_4Co(M^+—SbF_6{}^-)$ was 788.7434.

Complex Synthesis Example 2

Cobalt (II) acetate (tetrahydrate) (manufactured by Kishida Chemical Co., Ltd.) (124.5 mg, 0.5 mmol) was heated at 80° C., and dry in vacuum for one hour. After that, the resultant was returned to room temperature, and dissolved in dehydrated ethanol (5 ml) added in nitrogen flow.

Into ethanol (10 ml) was dissolved (1S,2S)-1,2-cyclohexane diamine (Kankyou Kagaku Center Co., Ltd.) (57.0 mg, 0.5 mmol). Into the solution was added 3,5-dibromosalicyl aldehyde (Tokyo Kasei Industries, Ltd.) (279.9 mg, 1.0 mmol). The solution was refluxed under heating and stirring for 6 hours. The reaction mixture was returned to room temperature after the completion of the reaction, and the precipitate formed was filtered and dried under heating for one hour. The dried precipitate was added to the above ethanol solution of the cobalt acetate, and the mixture was refluxed under heating for 6 hours. Then, the reaction mixture was returned to room temperature, and the precipitate was filtered in a nitrogen atmosphere, and dried by heating for one hour.

The dried precipitate was dissolved in dichloromethane in nitrogen atmosphere. Iodine (63.5 mg, 0.25 mmol) was added into the solution, which was stirred for one hour then, silver hexafluoroantimonate [Aldrich Chem. Co.](171.8 mg, 0.5 mmol) was added to the resultant, and the mixture was further stirred for one hour. After that, the reaction solution was filtered with Celite, and the filtrate was concentrated with a rotary evaporator, thereby removing dichloromethane. The residue was chromatographed in a silica gel column using dichloromethane/methanol (=20/1) as a developing solvent, thereby obtaining Co (III) (salen) complex having the following formula (X), that is, [(S,S)-N,N'-bis (3,5-dibromosalicylidene)-1,2-cyclohexane diaminate cobalt (III)]hexafluoroantimonate (311.3 mg, yield 89%).

[Formula (X)]

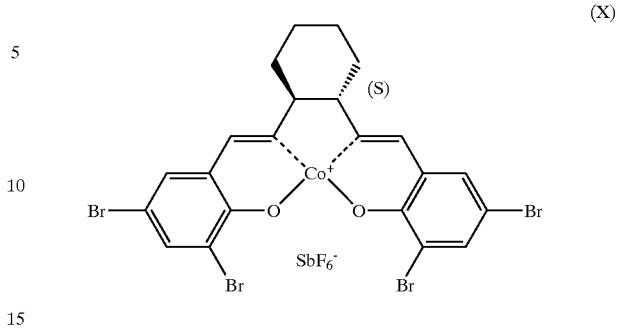

(X)

Results in IR (KBr) measurement of the complex obtained by the above method were 3065, 2937, 2862, 1637, 1581, 1516, 1441, 1377, 1344, 1315, 1290, 1165, 1034, 957, 868, 746, 715, 660, 586, 552, 511, 457 cm$^{-1}$. An actual measurement result of HRFAB-MS m/z was 690.7283, while the theoretical value of $C_{20}H_{16}O_2N_2{}^{79}Br_4Co(M^+—SbF_6{}^-)$ was 690.7277.

Complex Synthesis Example 3

Cobalt (II) acetate (tetrahydrate) (manufactured by Kishida Chemical Co., Ltd.) (124.5 mg, 0.5 mmol) was heated at 80° C., and dry in vacuum for one hour. Thereafter, the resultant was returned to room temperature, and dissolved in dehydrated ethanol (5 ml) added in nitrogen flow.

Into ethanol (10 ml) was suspended (R)-(+)-1,1'-binaphthyl-2,2'-diamine (Aldrich Chem. Co.) (142.2 mg, 0.5 mmol). Into the suspension was added 3,5-difluorosalicyl aldehyde (158.1 mg, 1.0 mmol) synthesized by reacting 3,5-difluorophenol with hexamethylene tetramine in trifluoroacetic acid (90° C.). The solution was refluxed under heating and stirring for 6 hours. The reaction mixture was returned to room temperature after the completion of the reaction, and the precipitate formed was filtered and dried under heating for one hour. The dried precipitate was added to the above ethanol solution of the cobalt acetate, and the mixture was refluxed under heating for 6 hours. Then, the reaction mixture was returned to room temperature, and ethanol was removed with the rotary evaporator and the residue was dried by heating for one hour.

The dried residue was dissolved in dichloromethane in nitrogen atmosphere. Iodine (63.5 mg, 0.25 mmol) was added into the solution, which was stirred for one hour. Then, dichloromethane was removed by using the rotary evaporator, and the residue was dried by heating for one hour, thereby obtaining Co (III) (salen) complex having the following formula (XI), that is, [(R)-N,N'-bis(3,5-difluorosalicylidene)-1,1'-binaphthyl-2,2'-diaminate cobalt (III)]iodide. This was utilized for an intended reaction without being isolated. A part of the product was taken for identification, which gave the following measurement results.

[Formula (XI)]

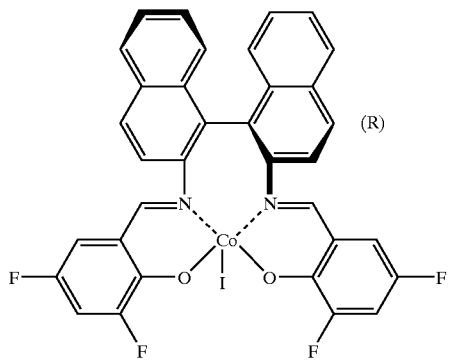

(XI)

Results in IR (KBr) measurement of the complex obtained by the above method were 3057, 1606, 1553, 1448, 1350, 1304, 1263, 1231, 1178, 1124, 1051, 991, 949, 825, 750, 694, 644 cm$^{-1}$. An actual measurement result of ESI-MS m/z was 620.9, while the theoretical value of $C_{34}H_{18}O_2N_2F_4Co(M^+-I^-)$ was 621.06.

Next, the Co(III) (salen) complex (374 mg, 0.5 mmol) having the above chemical formula (XI) was dissolved in dichloromethane, and silver hexafluoroantimonate [Aldrich Chem. Co.] (172.8 mg, 0.5 mmol) was added to the resultant, and the mixture was stirred for one hour. Then, the reaction solution was filtered with Celite, and the filtrate was concentrated with the rotary evaporator, thereby removing dichloromethane. The residue was chromatographed in a silica gel column using dichloromethane/methanol (=20/1) as a developing solvent, thereby obtaining Co (III) (salen) complex having the following formula (XII), that is, [(R)-N,N'-bis(3,5-difluorosalicylidene)-1,1'-binaphthyl-2,2'-diaminate cobalt (III)]hexafluoroantimonate (300.0 mg, yield 70%).

[Formula (XII)]

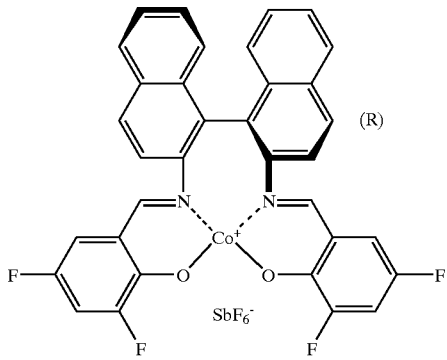

(XII)

Results in IR (KBr) measurement of the complex obtained by the above method were 3385, 3236, 3057, 2930, 1713, 1610, 1553, 1506, 1450, 1352, 1308, 1267, 1232, 1180, 1126, 1066, 989, 951, 831, 750, 694, 660, 582, 536, 488 cm$^{-1}$. An actual measurement result of HRFAB-MS m/z was 621.0641, while the theoretical value of $C_{34}H_{18}O_2N_2F_4Co(M^+-SbF_6^-)$ was 621.0636.

Complex Synthesis Example 4

Cobalt (II) acetate (tetrahydrate) (manufactured by Kishida Chemical Co., Ltd.) (124.5 mg, 0.5 mmol) was heated at 80° C., and dry in vacuum for one hour. Then, the resultant was returned to room temperature, and dissolved in dehydrated ethanol (5 ml) added in nitrogen flow.

Into ethanol (10 ml) was suspended (R)-(+)-1,1'-binaphthyl-2,2'-diamine (Aldrich Chem. Co.) (142.2 mg, 0.5 mmol). Into the suspension was added 3,5-difluorosalicyl aldehyde (158.1 mg, 1.0 mmol) synthesized by reacting 3,5-difluorophenol with hexamethylene tetramine in trifluoroacetic acid (90° C.). The solution was refluxed under heating and stirring for 6 hours. The reaction mixture was returned to room temperature after the completion of the reaction, and the precipitate formed was filtered and dried under heating for one hour. The dried precipitate was added to the above ethanol solution of the cobalt acetate, and the mixture was refluxed under heating for 6 hours. Thereafter, the reaction mixture was returned to room temperature, and ethanol was removed with the rotary evaporator and the residue was dried by heating for one hour.

The dried residue was dissolved in dichloromethane in nitrogen atmosphere. Bromine (40.0 mg, 0.25 mmol) was added into the solution, which was stirred for one hour. Then, dichloromethane was removed by using the rotary evaporator, and the residue was dried by heating for one hour, thereby obtaining Co (III) (salen) complex having the following formula (XIII), that is, [(R)-N,N'-bis(3,5-difluorosalicylidene)-1,1'-binaphthyl-2,2'-diaminate cobalt (III)]bromide. This was utilized for an intended reaction without being isolated. A part of the product was taken for identification, which gave the following measurement results.

[Formula (XIII)]

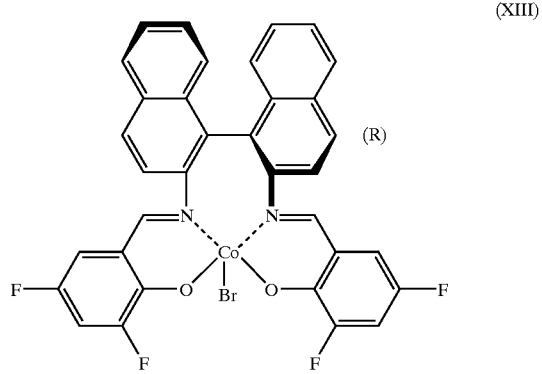

(XIII)

Results in IR (KBr) measurement of the complex obtained by the above method were 2964, 1612, 1585, 1560, 1468, 1389, 1327, 1271, 1227, 1180, 1126, 1070, 991, 925, 806, 748, 679 cm$^{-1}$. An actual measurement result of ESI-MS n/z was 620.9, while the theoretical value of $C_{34}H_{18}O_2N_2F_4Co(M^+—Br^-)$ was 621.06.

Complex Synthesis Example 5

Cobalt (II) acetate (tetrahydrate) (manufactured by Kishida Chemical Co., Ltd.) (124.5 mg, 0.5 mmol) was heated at 80° C., and dry in vacuum for one hour. Then, the resultant was returned to room temperature, and dissolved in dehydrated ethanol (5 ml) added in nitrogen flow.

Into ethanol (10 ml) was suspended (R)-(+)-1,1'-binaphthyl-2,2'-diamine (Aldrich Chem. Co.) (142.2 mg, 0.5 mmol). Into the suspension was added 3,5-dichlorosalicyl aldehyde (Tokyo Kasei Industries, Ltd.) (191.0 mg, 1.0 mmol). The solution was refluxed under heating and stirring for 6 hours. The reaction mixture was returned to room temperature after the completion of the reaction, and the precipitate formed was filtered and dried under heating for one hour. The dried precipitate was added to the above ethanol solution of the cobalt acetate, and the mixture was refluxed under heating for 6 hours. Then, the reaction mixture was returned to room temperature, and ethanol was removed with the rotary evaporator and the residue was dried by heating for one hour.

The dried residue was dissolved in dichloromethane in nitrogen atmosphere. Iodine (63.5 mg, 0.25 mmol) was added into the solution, which was stirred for one hour. Then, dichloromethane was removed by using the rotary evaporator, and the residue was dried by heating for one hour, thereby obtaining Co (III) (salen) complex having the following formula (XIV), that is, [(R)-N,N'-bis(3,5-difluorosalicylidene)-1,1'-binaphthyl-2,2'-diaminate cobalt (III)]iodide. This was utilized for an intended reaction without being isolated. A part of the product was taken for identification, which gave the following measurement results.

[Formula (XIV)]

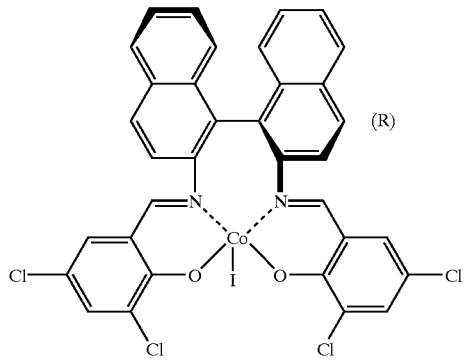

(XIV)

Results in IR (KBr) measurement of the complex obtained by the above method were 3059, 2930, 2374, 1603, 1508, 1433, 1379, 1306, 1200, 1163, 970, 864, 822, 748, 691 cm$^{-1}$. An actual measurement result of ESI-MS m/z was 684.8, while the theoretical value of $C_{34}H_{18}O_2N_2Cl_4Co(M^+—I^-)$ was 684.9.

Complex Synthesis Example 6

Cobalt (II) acetate (tetrahydrate) (manufactured by Kishida Chemical Co., Ltd.) (124.5 mg, 0.5 mmol) was heated at 80° C., and dry in vacuum for one hour. Then, the resultant was returned to room temperature, and dissolved in dehydrated ethanol (5 ml) added in nitrogen flow.

Into ethanol (10 ml) was suspended (R)-(+)-1,1'-binaphthyl-2,2'-diamine (Aldrich Chem. Co.) (142.2 mg, 0.5 mmol). Into the suspension was added 3,5-dibromosalicyl aldehyde (Tokyo Kasei Industries, Ltd.)(279.9 mg, 1.0 mmol). The solution was refluxed under heating and stirring for 6 hours. The reaction mixture was returned to room temperature after the completion of the reaction, and the precipitate formed was filtered and dried under heating for one hour. The dried precipitate was added to the above ethanol solution of the cobalt acetate, and the mixture was refluxed under heating for 6 hours. Thereafter, the reaction mixture was returned to room temperature, and the precipitate was filtered in nitrogen atmosphere and was dried by heating for one hour.

The dried precipitate was dissolved in dichloromethane in nitrogen atmosphere. Iodine (63.5 mg, 0.25 mmol) was added into the solution, which was stirred for one hour. Then, dichloromethane was removed by using the rotary evaporator, and the residue was dried by heating for one hour, thereby obtaining Co (III) (salen) complex having the following formula (XV), that is, [(R)-N,N'-bis(3,5-dibromosalicylidene)-1,1'-binaphthyl-2,2'-diaminate cobalt (III)]iodine. This was utilized for an intended reaction without being isolated. A part of the product was taken for identification, which gave the following measurement results.

[Formula (XV)]

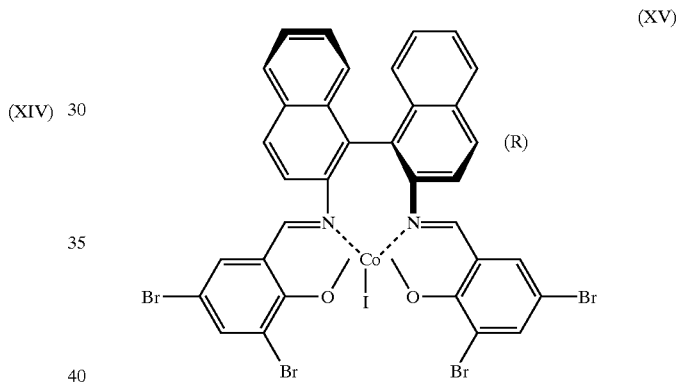

(XV)

Results in IR (KBr) measurement of the complex obtained by the above method were 3057, 3009, 2922, 1601, 1501, 1427, 1377, 1304, 1265, 1200, 1150, 1070, 1043, 955, 866, 818, 750, 714, 687, 658 cm$^{-1}$. An actual measurement result of ESI-MS m/z was 860.5, while the theoretical value of $C_{34}H_{18}O_2N_2{}^{79}Br_4Co(M^+—I^-)$ was 860.7.

Next, the Co(III) (salen) complex (496 mg, 0.5 mmol) having the above chemical formula (XV) was dissolved in dichloromethane, and silver hexafluoroantimonate [Aldrich Chem. Co.](172.8 mg, 0.5 mmol) was added to the resultant, and the mixture was stirred for one hour. Then, the reaction solution was filtered with Celite, and the filtrate was concentrated with the rotary evaporator, thereby removing dichloromethane. The residue was chromatographed in a silica gel column using dichloromethane/methanol (=20/1) as a developing solvent, thereby obtaining Co (III) (salen) complex having the following formula (XVI), that is, [(R)-N,N'-bis(3,5-dibromosalicylidene)-1,1'-binaphthyl-2,2'-diaminate cobalt (III)]hexafluoroantimonate (495.4 mg, yield 96%).

[Formula (XVI)]

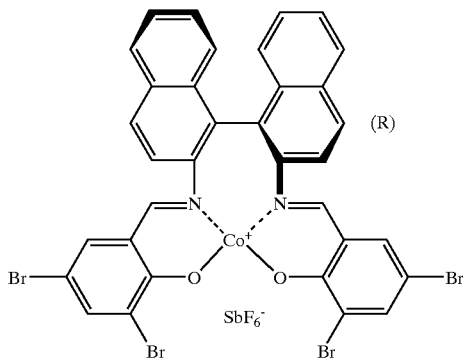

(XVI)

Results in IR (KBr) measurement of the complex obtained by the above method were 3381, 3290, 3230, 3059, 3014, 2924, 2854, 1601, 1504, 1431, 1367, 1306, 1265, 1203, 1161, 1092, 951, 864, 820, 777, 750, 723, 662, 540, 496, 438 cm$^{-1}$. An actual measurement result of HRFAB-MS m/z was 860.7443, while the theoretical value of $C_{34}H_{18}O_2N_2{}^{79}Br_4Co(M^+-SbF_6^-)$ was 860.7434.

Complex Synthesis Example 7

Cobalt (II) acetate (tetrahydrate) (manufactured by Kishida Chemical Co., Ltd.) (124.5 mg, 0.5 mmol) was heated at 80° C., and dry in vacuum for one hour. Then, the resultant was returned to room temperature, and dissolved in dehydrated ethanol (5 ml) added in nitrogen flow.

Into ethanol (10 ml) was suspended (R)-(+)-1,1'-binaphthyl-2,2'-diamine (Aldrich Chem. Co.) (142.2 mg, 0.5 mmol). Into the suspension was added 3,5-diiodosalicyl aldehyde (Tokyo Kasei Industries, Ltd.) (373.9 mg, 1.0 mmol). The solution was refluxed under heating and stirring for 6 hours. The reaction mixture was returned to room temperature after the completion of the reaction, and the precipitate formed was filtered and dried under heating for one hour. The dried precipitate was added to the above ethanol solution of the cobalt acetate, and the mixture was refluxed under heating for 6 hours. Thereafter, the reaction mixture was returned to room temperature, ethanol was removed by using the rotary evaporator, and the residue was dried by heating for one hour.

The dried residue was dissolved in dichloromethane in nitrogen atmosphere. Iodine (63.5 mg, 0.25 mmol) was added into the solution, which was stirred for one hour. Then, dichloromethane was removed by using the rotary evaporator, and the residue was dried by heating for one hour, thereby obtaining Co (III) (salen) complex having the following formula (XVII), that is, [(R)-N,N'-bis(3,5-diiodosalicylidene)-1,1'-binaphthyl-2,2'-diaminate cobalt (III)]iodine. This was utilized for an intended reaction without being isolated. A part of the product was taken for identification, which gave the following measurement results.

[Formula (XVII)]

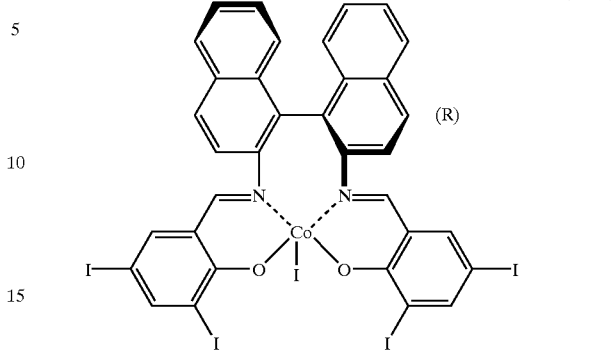

(XVII)

Results in IR (KBr) measurement of the complex obtained by the above method were 3051, 2923, 2301, 1595, 1487, 1421, 1371, 1302, 1204, 1146, 1113, 1072, 955, 864, 814, 748, 679 cm$^{-1}$. An actual measurement result of ESI-MS m/z was 1052.5, while the theoretical value of $C_{34}H_{18}O_2N_2I_4Co(M^+-I^-)$ was 1052.7.

Complex Synthesis Example 8

Into ethanol (7 ml) was suspended (R)-1,1'-binaphthyl-2,2'-diamine (Aldrich Chem. Co.) (200 mg, 0.7 mmol). Into the suspension was added 3-tert.-butyl-5-nitrosalicyl aldehyde (314 mg, 1.4 mmol) synthesized by treating 3-tert.-butylsalicyl aldehyde (Aldrich Chem., Co.) with a mixture of conc. nitric acid and conc. sulfuric acid. The solution was heated at 90° C. under stirring for 12 hours. Then, the reaction mixture was returned to room temperature, and the precipitate was filtered and was dried under vacuum.

Cobalt (II) acetate (tetrahydrate) (manufactured by Kishida Chemical Co., Ltd.) was heated at 70–80° C. in vacuum until its color changed from pink to purple, and the resulting cobalt (II) acetate (50 mg, 0.2 mmol) was added and dissolved into deaerated N,N'-dimethylformamide (DMF) (4 ml). Into this solution was added the above precipitate (139 mg, 0.2 mmol), which was heated at 110° C. for 24 hours and then concentrated in vacuum. Thereafter, the resultant was dissolved into dichloromethane (4 ml). Into this solution was added iodine (25.4 mg, 0.1 mmol), which was stirred for one hour. Then, the mixed liquid was concentrated, and the residue was chromatographed in a silica gel column using hexane/dichloromethane (=1/0 to 1/1) as a developing solvent, thereby obtaining Co (III) (salen) complex having the following formula (XVIII), that is, [(R)-N,N'-bis(3-tert.-butyl-5-nitrosalicylidene)-1,1'-binaphthyl-2,2'-diaminate cobalt (III)]iodine (113 mg, yield 64%).

[Formula (XVIII)]

(XVIII)

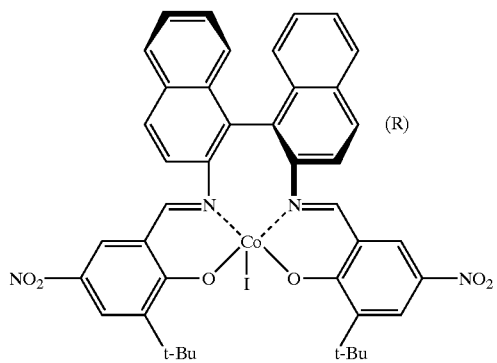

Results in IR (KBr) measurement of the complex obtained by the above method were 3059, 2957, 2916, 2870, 1593, 1554, 1500, 1470, 1419, 1387, 1315, 1200, 1173, 1115, 1076, 1028, 984, 922, 866, 829, 798, 739, 681, 561, 509, 484 cm$^{-1}$. An actual measurement result of HRFAB-MS m/z was 751.1971, while the theoretical value of $C_{42}H_{36}O_6N_4Co$ (M$^+$—I$^-$) was 751.1967.

Complex Synthesis Example 9

Cobalt (II) acetate (tetrahydrate) (manufactured by Kishida Chemical Co., Ltd.) (124.5 mg, 0.5 mmol) was heated at 80° C., and dry in vacuum for one hour. Then, the resultant was returned to room temperature, and dissolved in dehydrated ethanol (5 ml) added in nitrogen flow.

Into ethanol (10 ml) was suspended (R)-(+)-1,1'-binaphthyl-2,2'-diamine (Aldrich Chem. Co.) (142.2 mg, 0.5 mmol). Into the suspension was added salicyl aldehyde (Nakarai Tesc Co., Ltd.) (122.1 mg, 1.0 mmol). The solution was refluxed under heating and stirring for 6 hours. The reaction mixture was returned to room temperature after the completion of the reaction, and the precipitate formed was filtered and dried under heating for one hour. The dried precipitate was added to the above ethanol solution of the cobalt acetate, and the mixture was refluxed under heating for 6 hours. Thereafter, the reaction mixture was returned to room temperature, and the precipitate was filtered in nitrogen atmosphere and dried by heating for one hour.

The dried precipitate was dissolved in dichloromethane in nitrogen atmosphere. Iodine (63.5 mg, 0.25 mmol) was added into the solution, which was stirred for one hour. Then, silver hexafluoroantimonate (Aldrich Chem. Co., Ltd.) (172.8 mg, 0.5 mmol) was added to the solution, which was further stirred for one hour. After that, the reaction solution was filtered with Celite, and the filtrate was concentrated with the rotary evaporator, thereby removing dichloromethane. The residue was subjected to separation with a silica gel column using dichloromethane/methanol (=20/1) as a developing solvent, thereby obtaining Co (III) (salen) complex having the following formula (XIX), that is, [(R)-N,N'-bis(salicylidene)-1,1'-binaphthyl-2,2'-diaminate cobalt (III)]hexafluoroantimonate (325.9 mg, yield 83%).

[Formula (XIX)]

(XIX)

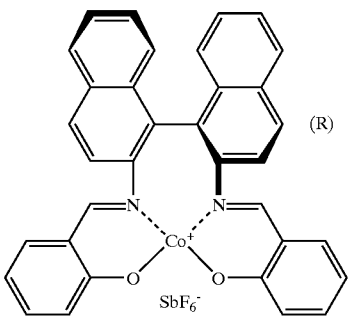

Results in IR (KBr) measurement of the complex obtained by the above method were 3298, 3236, 3055, 3014, 2926, 1607, 1527, 1441, 1375, 1313, 1190, 1149, 1074, 957, 910, 816, 752, 660, 492, 440 cm$^{-1}$. An actual measurement result of HRFAB-MS m/z was 549.1012, while the theoretical value of $C_{34}H_{22}O_2N_2Co$(M$^+$—SBF$_6^-$) was 549.1013.

Complex Synthesis Example 10

Cobalt (II) acetate (tetrahydrate) (manufactured by Kishida Chemical Co., Ltd.) (124.5 mg, 0.5 mmol) was heated at 80° C., and dry in vacuum for one hour. Thereafter, the resultant was returned to room temperature, and dissolved in dehydrated ethanol (5 ml) added in nitrogen flow.

Into ethanol (10 ml) was suspended (R)-(+)-1,1'-binaphthyl-2,2'-diamine (Aldrich Chem. Co.) (142.2 mg, 0.5 mmol). Into the suspension was added 2-hydroxy-5-methoxybenzaldehyde (Aldrich Chem. Co.) (152.2 mg, 1.0 mmol). The solution was refluxed under heating and stirring for 6 hours. The reaction mixture was returned to room temperature after the completion of the reaction, ethanol was removed by using the rotary evaporator, and the residue was dried under heating for one hour. The dried residue was added to the above ethanol solution of the cobalt acetate, and the mixture was refluxed under heating for 6 hours. Thereafter, the reaction mixture was returned to room temperature, and the precipitate was filtered in nitrogen atmosphere and dried by heating for one hour.

The dried precipitate was dissolved in dichloromethane in nitrogen atmosphere. Iodine (63.5 mg, 0.25 mmol) was added into the solution, which was stirred for one hour. Then, silver hexafluoroantimonate (Aldrich Chem. Co.) (172.8 mg, 0.5 mmol) was added to the solution, which was further stirred for one hour. After that, the reaction solution was filtered with Celite, and the filtrate was concentrated with the rotary evaporator, thereby removing dichloromethane. The residue was chromatographed in a silica gelcolumn using dichloromethane/methanol (=20/1) as a developing solvent, thereby obtaining Co (III) (salen) complex having the following formula (XX), that is, [(R)-N,N'-bis(5-dimethoxysalicylidene)-1,1'-binaphthyl-2,2'-diaminate cobalt (III)]hexafluoroantimonate (367.7 mg, yield 87%).

[Formula (XX)]

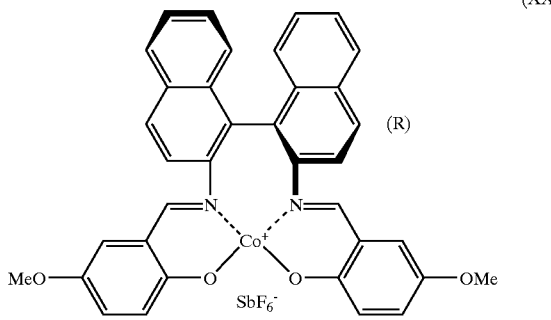

Results in IR (KBr) measurement of the complex obtained by the above method were 3385, 3302, 3238, 3055, 3001, 2937, 2837, 1593, 1533, 1510, 1462, 1431, 1356, 1302, 1267, 1219, 1155, 1076, 1036, 947, 818, 750, 660, 575, 527, 494, 440 cm$^{-1}$. An actual measurement result of HRFAB-MS m/z was 606.1225, while the theoretical value of $C_{36}H_{26}O_4N_2Co(M^+\text{—}SbF_6^-)$ was 609.1225.

Example 1

Into 0.5 ml of dichloromethane ($CH_2Cl_2$) was dissolved 3-phenylcyclobutanone (14.6 mg, 0.1 mmol) at room temperature. Into this dichloromethane solution was added the Co(III) (salen) complex (5.5 mg, 5.0 µmol) having the above formula (XVI). Into this solution was added 30% hydrogen peroxide aqueous solution (15 µl, content of hydrogen peroxide 0.13 mmol), which was stirred at room temperature for 24 hours. After the completion of the reaction, the dichloromethane was removed by the rotary evaporator, and the residue was chromatographed in a silica gel column using hexane/ethyl acetate (=45/7) as a developing solvent, thereby obtaining β-phenyl-γ-butylolactone (4.9 mg, yield 30%). Analysis of the enatiomer excess percentage of this lactone by high liquid chromatography with a Daicel Chiralpak AD-H column using an eluting liquid of hexane/isopropanol (=49/1) revealed that the product was composed mainly of the S isomer, and its enantiomeric excess percentage was 20% ee. Results are shown in Table 1.

Example 2

Example 2 was effected in the same manner as in Example 1 except that urea-hydrogen peroxide adduct (UHP) (12 mg, content of hydrogen peroxide 0.13 mmol) was used instead of 30% hydrogen peroxide aqueous solution (15 µl, content of hydrogen peroxide 0.13 mmol). Results are shown in Table 1.

Example 3

Example 3 was effected in the same manner as in Example 2 except that the Co(III) (salen) complex (4.3 mg, 5.0 µmol) having the formula (XII) was used instead of the Co(III) (salen) complex (5.5 mg, 5.0 µmol) having the formula (XVI). Results are shown in Table 1.

Example 4

Example 4 was effected in the same manner as in Example 2 except that the Co(III) (salen) complex (3.9 mg, 5.0 µmol) having the formula (XIX) was used instead of the Co(III) (salen) complex (5.5 mg, 5.0 µmol) having the formula (XVI). Results are shown in Table 1.

Reference Example 1

Reference Example 1 was effected in the same manner as in Example 1 except that the Co(III) (salen) complex (5.1 mg, 5.0 µmol) having the formula (IX) was used instead of the Co(III) (salen) complex (5.5 mg, 5.0 µmol) having the formula (XVI). Results are shown in Table 1.

Reference Example 2

Reference Example 1 was effected in the same manner as in Example 1 except that a toluene solution (3.34 N) of t-butylhydroperoxide (TBHP) (30 µl, TBHP content 0.1 mmol) was used instead of used instead of 30% hydrogen peroxide aqueous solution (15 µl, content of hydrogen peroxide 0.13 mmol). Results are shown in Table 1.

Reference Example 3

Into 0.5 ml of dichloromethane ($CH_2Cl_2$) was dissolved 3-phenyl cyclobutane (14.6 mg, 0.1 mmol). Into this dichloromethane solution was added the Co(III) (salen) complex (5.1 mg, 5.0 µmol) having the above formula (IX), which was cooled to −78° C. Into the resulting solution were added methachloro perbenzoic acid (m-CPBA) (26 mg, 0.1 mmol) and N-methyl morpholine-N-oxide (12 mg, 0.1 mmol), which was stirred at −78° C. for 24 hours. Then, β-phenyl-γ-butylolactone was separated and analyzed in the same manner as in Example 1. Results are shown in Table 1.

Reference Example 4

Reference Example 4 was effected in the same manner as in Reference Example 1 except that the Co(III) (salen) complex (4.7 mg, 5.0 µmol) having the formula (X) was used instead of the Co(III) (salen) complex (5.1 mg, 5.0 µmol) having the formula (IX). Results are shown in Table 1.

Reference Example 5

Reference Example 5 was effected in the same manner as in Reference Example 2 except that the Co(III) (salen) complex (4.7 mg, 5.0 µmol) having the formula (X) was used instead of the Co(III) (salen) complex (5.1 mg, 5.0 µmol) having the formula (IX). Results are shown in Table 1.

Reference Example 6

Reference Example 6 was effected in the same manner as Reference Example 3 except that the Co(III) (salen) complex (4.7 mg, 5.0 µmol) having the formula (X) was used instead of the Co(III) (salen) complex (5.1 mg, 5.0 µmol) having the formula (IX). Results are shown in Table 1.

Reference Example 7

Reference Example 7 was effected in the same manner as in Reference Example 2 except that the Co(III) (salen) complex (5.5 mg, 5.0 µmol) having the formula (XVI) was used instead of the Co(III) (salen) complex (5.1 mg, 5.0 µmol) having the formula (IX). Results are shown in Table 1.

Reference Example 8

Reference Example 8 was effected in the same manner as in Reference Example 3 except that the Co(III) (salen) complex (5.5 mg, 5.0 µmol) having the formula (XVI) was used instead of the Co(III) (salen) complex (5.1 mg, 5.0 µmol) having the formula (IX). Results are shown in Table 1.

Reference Example 9

Reference Example 9 was effected in the same manner as in Reference Example 2 except that the Co(III) (salen) complex (4.3 mg, 5.0 μmol) having the formula (XX) was used instead of the Co(III) (salen) complex (5.1 mg, 5.0 μmol) having the formula (IX). Results are shown in Table 1.

TABLE 1

| catalyst | oxidant | yielded (mg) | yield (%) | enantiomeric excess percentage (% ee) (*) | configuration (**) |
|---|---|---|---|---|---|
| Example 1 formula (XVI) | $H_2O_2$ | 4.9 | 30 | 20 | S |
| Example 2 formula (XVI) | UHP | 5.0 | 31 | 53 | S |
| Example 3 formula (XII) | UHP | 4.9 | 30 | 57 | S |
| Example 4 formula (XIX) | UHP | 1.6 | 10 | 55 | S |
| Reference Example 1 formula (IX) | $H_2O_2$ | 4.7 | 29 | 0 | rasemi |
| Reference Example 2 formula (IX) | TBHP | 11.7 | 72 | 0 | rasemi |
| Reference Example 3 formula (IX) | m-CPBA | 13.2 | 75 | 0 | rasemi |
| Reference Example 4 formula (X) | $H_2O_2$ | 3.2 | 20 | 0 | rasemi |
| Reference Example 5 formula (X) | TBHP | 10 | 62 | 0 | rasemi |
| Reference Example 6 formula (X) | m-CPBA | 13 | 80 | 0 | rasemi |
| Reference Example 7 formula (XVI) | TBHP | 4.4 | 27 | 0 | rasemi |
| Reference Example 8 formula (XVI) | m-CPBA | 12.6 | 78 | 0 | rasemi |
| Reference Example 9 formula (XX) | UHP | 0 | 0 | — | — |

(*) The enantiomeric excess percentage (% ee) was determined by HPLC.
(**) The absolute conformation was determined by chiroptical comparison.

For example, the specific optical rotation of the S isomer of β-phenyl-γ-butylolactone is $[\alpha]^{20}_D = +50.5°$ (c 5, MeOH) at 20° C., whereas the specific optical rotation of β-phenyl-γ-butylolactone is $[\alpha]^{24}_D = +37.0°$ (c 0.53, MeOH) at 24° C.

The reaction formula corresponding to Examples 1 to 4 and Reference Examples 1 to 9 in Table 1 is shown below.

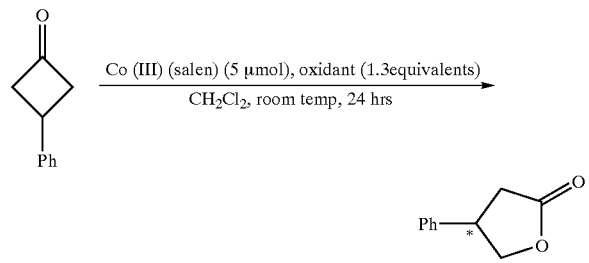

It is seen from Table 1 that the cationic cobalt(salen) complexes having the formulae (XVI),(XII) and (XIX) are more excellent as the catalysts in terms of the enantiomeric excess percentage. Further, it is seen that $H_2O_2$ and UHP are more excellent in terms of the enatiomer excess percentage.

Example 5

Example 5 was effected in the same manner as in Example 3 except that tetrahydrofuran (THF) (0.5 ml) was used instead of dichloromethane ($CH_2Cl_2$) (0.5 ml). Results are shown in Table 2.

Example 6

Example 6 was effected in the same manner as in Example 3 except that acetonitrile ($CH_3CN$) (0.5 ml) was used instead of dichloromethane ($CH_2Cl_2$) (0.5 ml). Results are shown in Table 2.

Example 7

Example 7 was effected in the same manner as in Example 3 except that ethanol (EtOH) (0.5 ml) was used instead of dichloromethane ($CH_2Cl_2$) (0.5 ml). Results are shown in Table 2.

Example 8

Example 8 was effected in the same manner as in Example 7 except that 30% hydrogen peroxide ($H_2O_2$) aqueous solution (15 μl, hydrogen peroxide content 0.13 mmol) was used instead of urea-hydrogen peroxide adduct (UHP) (12 mg, hydrogen peroxide content 0.13 mmol). Results are shown in Table 2.

Example 9

Into 0.5 ml of ethanol (EtOH) was dissolved 3-phenyl cyclobutane (14.6 mg, 0.1 mmol). Into this ethanol solution was added the Co(III) (salen) complex (4.3 mg, 5.0 μmol) having the above formula (XII), which was cooled to 0° C. Into the resulting solution was added urea-hydrogen peroxide adduct (12 mg, hydrogen peroxide content 0.13 mmol), which was stirred at 0° C. for 24 hours. Then, β-phenyl-γ-butylolactone was separated and analyzed in the same manner as in Example 1. Results are shown in Table 2.

Example 10

Example 10 was effected in the same manner as in Example 9 except that 30% hydrogen peroxide ($H_2O_2$) aqueous solution (15 μl, hydrogen peroxide content 0.13 mmol) was used instead of urea-hydrogen peroxide adduct (UHP) (12 mg, hydrogen peroxide content 0.13 mmol). Results are shown in Table 2.

Example 11

Into 0.5 ml of ethanol (EtOH) was dissolved 3-phenyl cyclobutane (14.6 mg, 0.1 mmol). Into this ethanol solution was added the Co(III) (salen) complex (4.3 mg, 5.0 μmol) having the above formula (XII), which was cooled to −20° C. Into the resulting solution was added hydrogen peroxide (15 μl, hydrogen peroxide content 0.13 mmol), which was stirred at −20° C. for 24 hours. Then, β-phenyl-γ-butylolactone was separated and analyzed in the same manner as in Example 1. Results are shown in Table 2.

Example 12

Into 0.5 ml of ethanol (EtOH) was dissolved 3-phenyl cyclobutane (14.6 mg, 0.1 mmol). Into this ethanol solution was added the Co(III) (salen) complex (4.3 mg, 5.0 μmol) having the above formula (XII), which was cooled to −78° C. Into the resulting solution was added urea-hydrogen peroxide adduct (12 mg, hydrogen peroxide content 0.13 mmol), which was stirred at −78° C. for 24 hours. Then, β-phenyl-γ-butylolactone was separated and analyzed in the same manner as in Example 1. Results are shown in Table 2.

Example 13

Example 13 was effected in the same manner as in Example 3 except that methanol (MeOH) (0.5 ml) was used instead of dichloromethane (CH$_2$Cl$_2$) (0.5 ml). Results are shown in Table 2.

Example 14

Example 14 was effected in the same manner as in Example 3 except that isopropanol (i-PrOH) (0.5 ml) was used instead of dichloromethane (CH$_2$Cl$_2$) (0.5 ml). Results are shown in Table 2.

Example 15

Example 13 was effected in the same manner as in Example 3 except that ethyl acetate (AcOEt) (0.5 ml) was used instead of dichloromethane (CH$_2$Cl$_2$) (0.5 ml). Results are shown in Table 2.

Example 16

Example 16 was effected in the same manner as in Example 3 except that diethyl ether (Et$_2$O) (0.5 ml) was used instead of dichloromethane (CH$_2$Cl$_2$) (0.5 ml). Results are shown in Table 2.

Example 17

Example 17 was effected in the same manner as in Example 3 except that hexane (MeOH) (0.5 ml) was used instead of dichloromethane (CH$_2$Cl$_2$) (0.5 ml). Results are shown in Table 2.

Example 18

Example 18 was effected in the same manner as in Example 3 except that methanol benzene (0.5 ml) was used instead of dichloromethane (CH$_2$Cl$_2$) (0.5 ml). Results are shown in Table 2.

Example 19

Example 19 was effected in the same manner as in Example 3 except that toluene (0.5 ml) was used instead of dichloromethane (CH$_2$Cl$_2$) (0.5 ml). Results are shown in Table 2.

The reaction formula corresponding to Examples 5 to 19 in Table 2 is shown below.

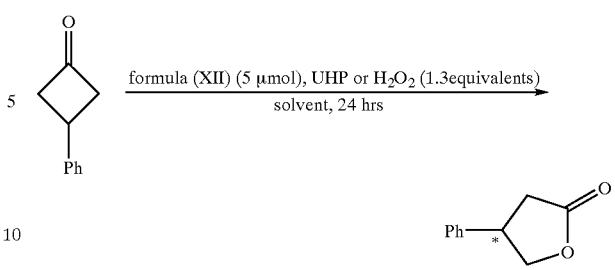

It is seen from Table 2 that tetrahydrofuran (THF), acetonitrile, ethanol, methanol, isopropanol, ethyl acetate and diethyl ether are more excellent as the solvent in terms of the enantiomeric excess percentage. Further, it is seen that the reaction temperature range of −20 to 0° C. is more excellent in terms of the enantiomeric excess percentage.

Example 20

Asymmetric Baeyer-Villiger oxidation of 3-(p-chlorophenyl)cyclobutanone

Into 0.5 ml of ethanol was dissolved 3-(p-chlorophenyl) cyclobutanone (18.0 mg, 0.1 mmol). Into this ethanol solution was added the Co(III) (salen) complex (4.3 mg, 5.0 μmol) having the above formula (XII). Into this solution was added 30% hydrogen peroxide aqueous solution (15 μl, content of hydrogen peroxide 0.13 mmol), which was stirred at 0° C. for 24 hours. After the completion of the reaction, the ethanol was removed by the rotary evaporator, and the residue was chromatographed in a silica gel column using hexane/ethyl acetate (=45/7) as a developing solvent, thereby obtaining β-(p-chlorophenyl)-γ-butylolactone (14.9 mg, yield 76%). Analysis of the enatiomer excess percentage of this lactone by high liquid chromatography with a Daicel Chiralpak AD-H column using an eluting liquid of hexane/isopropanol (=49/1) revealed that the product was composed mainly of the S isomer, and its enantiomeric excess percentage was 75% ee.

The absolute conformation was determined through the chiproptical comparison. For example, the specific optical rotation of the S isomer of β-(p-chlorophenyl)-γ-butylolactone is $[\alpha]_D$=+46.5°(c 0.5, CHCl$_3$) at 20° C.,

TABLE 2

| | oxidant | solvent | reaction temperature (° C.) | yielded (mg) | yield (%) | enantiomeric excess percentage (% ee) | configuration (*) |
|---|---|---|---|---|---|---|---|
| Example 3 | UHP | CH$_2$Cl$_2$ | Room temp. | 4.9 | 30 | 57 | S |
| Example 5 | UHP | THF | Room temp. | 11 | 69 | 70 | S |
| Example 6 | UHP | CH$_3$CN | Room temp. | 15.1 | 93 | 67 | S |
| Example 7 | UHP | EtOH | Room temp. | 14.1 | 87 | 71 | S |
| Example 8 | H$_2$O$_2$ | EtOH | Room temp. | 14.9 | 92 | 69 | S |
| Example 9 | UHP | EtOH | 0° C. | 14.6 | 90 | 75 | S |
| Example 10 | H$_2$O$_2$ | EtOH | 0° C. | 13.8 | 85 | 75 | S |
| Example 11 | H$_2$O$_2$ | EtOH | −20° C. | 11.7 | 72 | 77 | S |
| Example 12 | UHP | EtOH | −78° C. | 13.9 | 86 | 69 | S |
| Example 13 | UHP | MeOH | Room temp. | 13.6 | 84 | 70 | S |
| Example 14 | UHP | i-PrOH | Room temp. | 14.9 | 92 | 71 | S |
| Example 15 | UHP | AcOEt | Room temp. | 14.1 | 87 | 60 | S |
| Example 16 | UHP | Et$_2$O | Room temp. | 13.4 | 83 | 69 | S |
| Example 17 | UHP | hexane | Room temp. | 12.6 | 78 | 50 | S |
| Example 18 | UHP | benzene | Room temp. | 3.6 | 22 | 55 | S |
| Example 19 | UHP | toluene | Room temp. | 4.1 | 25 | 55 | S |

In Examples of Table 2, the complex of the formula (XII) was used as the catalyst.
(*) Absolute conformation was determined by chiroptical comparison.

whereas the specific optical rotation of the β-(p-chlorophenyl)-γ-butylolactone is [α]$_D$=+39.8°(c 0.47, CHCl$_3$) at 24° C. Thus, the absolute conformation was the S isomer. The reaction formula was shown below.

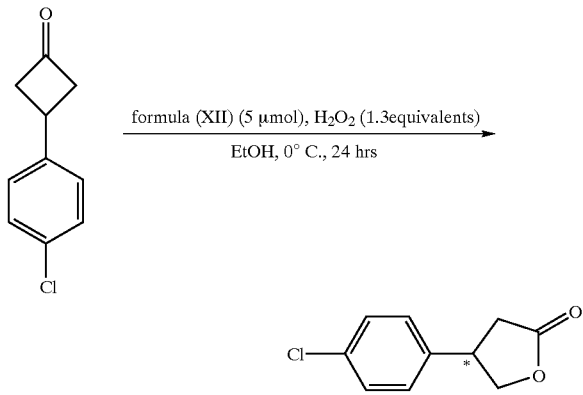

Example 21

Asymmetric Baeyer-Villiger oxidation of 3-(p-methoxyphenyl)cyclobutanone

Into 0.5 ml of ethanol was dissolved 3-(p-methoxyphenyl) cyclobutanone (17.6 mg, 0.1 mmol). Into this ethanol solution was added the Co(III) (salen) complex (4.3 mg, 5.0 μmol) having the above formula (XII). Into this solution was added 30% hydrogen peroxide aqueous solution (15 μl, content of hydrogen peroxide 0.13 mmol), which was stirred at 0° C. for 24 hours. After the completion of the reaction, the ethanol was removed by the rotary evaporator, and the residue was chromatographed in a silica gel column using hexane/ethyl acetate (=45/7) as a developing solvent, thereby obtaining β-(p-methoxyphenyl)-γ-butylolactone (14.5 mg, yield 75%). Analysis of the enatiomer excess percentage of this lactone by high liquid chromatography with a Daicel Chiralpak AD-H column using an eluting liquid of hexane/isopropanol (=49/1) revealed that the product was composed mainly of the S isomer, and its enantiomeric excess percentage was 78% ee. The reaction formula is shown below.

(β-(p-methoxyphenyl)-γ-butylolactone): $^1$H NMR(400 MHz): δ7.15(d, J=8.5 Hz, 2H), 6.90(d, J=8.5 Hz, 2H), 4.63(dd, J=7.8, 9.0 Hz, 1H), 4.22(dd, J=8.2, 9.0 Hz, 1H), 3.81(s, 3H), 3.78–3.69(m, 1H), 2.89(dd, J=8.7, 17.6 Hz, 1H), 2.63(dd, J=9.3, 17.6 Hz, 1H). IR(KBr method): 3527, 3454, 3014, 2962, 2904, 1774, 1483, 1356, 1300, 1167, 1092, 1011, 905, 833, 681, 590, 542, 501, 455 cm$^{-1}$.

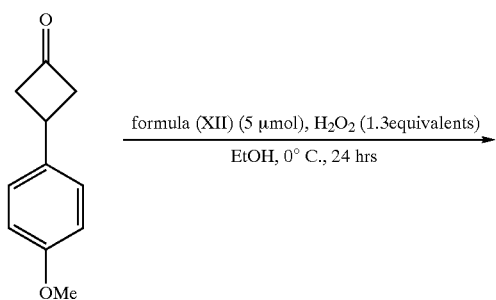

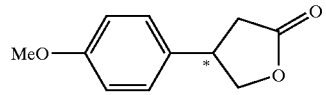

Example 22

Asymmetric Baeyer-Villiger oxidation of 3-octylcyclobutanone

Into 0.5 ml of ethanol (EtOH) was dissolved 3-octylcyclobutanone (18.2 mg, 0.1 mmol). Into this ethanol solution was added the Co(III) (salen) complex (4.3 mg, 5.0 μmol) having the above formula (XII). Into this solution was added 30% hydrogen peroxide aqueous solution (15 μl, content of hydrogen peroxide 0.13 mmol), which was stirred at 0° C. for 24 hours. After the completion of the reaction, the ethanol was removed by the rotary evaporator, and the residue was chromatographed in a silica gel column using hexane/ethyl acetate (=45/7) as a developing solvent, thereby obtaining β-octyl-γ-butylolactone (14.9 mg, yield 75%). Analysis of the enatiomer excess percentage of this lactone by the proton nuclear magnetic resonance spectrum ($^1$H NMR) with a shift reagent revealed that its enantiomeric excess percentage was 73% ee. The reaction formula is shown below.

(β-octyl-γ-butylolactone) $^1$HNMR(4000 MHz): δ4.41(dd, J=8.8 and 7.3 Hz, 1H), 3.92(dd, J=8.8 and 7.1 Hz, 1H), 2.61(dd, J=16.6 and 8.3 Hz, 1H), 2.54(ddd, J=8.3, 7.6 and 7.3 Hz, 1H), 2.17(dd, J=16.6 and 7.6 Hz, 1H), 2.20–2.15 (m, 2H), 1.32–1.26(m, 10H), 0.88(t, J=7.8 Hz, 3H). IR(liquid film method): 2924, 2854, 1780, 1462, 1421, 1377, 1259, 1169, 1020, 798 cm$^{-1}$.

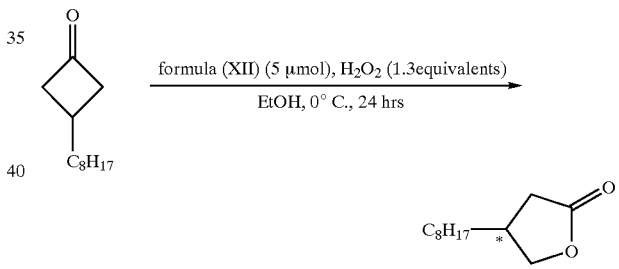

It is seen from Examples 21, 22 and 23 that the cationic cobalt(salen) complexes according to the present invention are effective for the Baeyer-Villiger oxidation of various chiral cyclic ketone compounds.

Example 23

Example 23 was effected in the same manner as in Example 7 except that the Co (III) (salen) complex having the formula (XIII) (3.5 mg, 5.0 μmol) was used instead of the Co (III) (salen) complex having the formula (XII) (4.3 mg, 5.0 μmol). Results are shown in Table 3.

Example 24

Example 24 was effected in the same manner as in Example 7 except that the Co (III) (salen) complex having the formula (XI) (3.7 mg, 5.0 μmol) was used instead of the Co (III) (salen) complex having the formula (XII) (4.3 mg, 5.0 μmol). Results are shown in Table 3.

Example 25

Example 25 was effected in the same manner as in Example 24 except that tetrahydrofuran (THF) (0.5 ml) was used instead of ethanol (EtOH) (0.5 ml). Results are shown in Table 3.

Example 26

Example 26 was effected in the same manner as in Example 24 except that acetonitrile (CH₃CN) (0.5 ml) was used instead of ethanol (EtOH) (0.5 ml). Results are shown in Table 3.

Example 27

Example 27 was effected in the same manner as in Example 24 except that ethyl acetate (AcOEt) (0.5 ml) was used instead of ethanol (EtOH) (0.5 ml). Results are shown in Table 3.

Example 28

Example 28 was effected in the same manner as in Example 24 except that diethyl ether (Et₂O) (0.5 ml) was used instead of ethanol (EtOH) (0.5 ml). Results are shown in Table 3.

Example 29

Example 29 was effected in the same manner as in Example 24 except that hexane (0.5 ml) was used instead of ethanol (EtOH) (0.5 ml). Results are shown in Table 3.

Example 30

Example 30 was effected in the same manner as in Example 24 except that benzene (0.5 ml) was used instead of ethanol (EtOH) (0.5 ml). Results are shown in Table 3.

Example 31

Example 31 was effected in the same manner as in Example 24 except that toluene (0.5 ml) was used instead of ethanol (EtOH) (0.5 ml). Results are shown in Table 3.

Example 32

Example 32 was effected in the same manner as in Example 24 except that dichloromethane (CH₂Cl₂) (0.5 ml) was used instead of ethanol (EtOH) (0.5 ml). Results are shown in Table 3.

TABLE 3

| | catalyst | solvent | yield (%) | enantiomeric excess percentage (% ee) | configu-ration |
|---|---|---|---|---|---|
| Example 7 | formula (XII) | EtOH | 87 | 71 | S |
| Example 23 | formula (XIII) | EtOH | 70 | 26 | S |
| Example 24 | formula (XI) | EtOH | 97 | 72 | S |
| Example 25 | formula (XI) | THF | 52 | 71 | S |
| Example 26 | formula (XI) | CH₃CN | 62 | 65 | S |
| Example 27 | formula (XI) | AcOEt | 75 | 71 | S |
| Example 28 | formula (XI) | Et₂O | 71 | 69 | S |
| Example 29 | formula (XI) | hexane | 45 | 54 | S |
| Example 30 | formula (XI) | benzene | 21 | 66 | S |
| Example 31 | formula (XI) | toluene | 25 | 64 | S |
| Example 32 | formula (XI) | CH₂Cl₂ | 43 | 69 | S |

The reaction formula corresponding to Examples 23 to 32 in Table 3 is shown below.

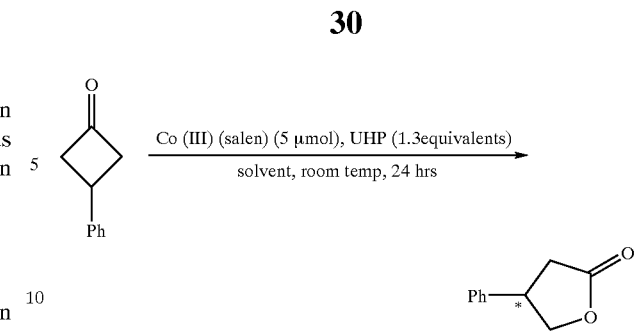

It is seen from Table 3 that the complexes corresponding to the precursors of the cationic cobalt(salen) complexes are effective for the asymmetric Baeyer-Villiger oxidation of the cyclic ketone compounds.

Example 33

Example 33 was effected in the same manner as in Example 10 except that the Co (III) (salen) complex (3.7 mg, 5.0 μmol) having the above formula (XI) (3.7 mg, 5.0 μmol) was used instead of the Co (III) (salen) complex (4.3 mg, 5.0 μmol) having the above formula (XII) (4.3 mg, 5.0 μmol). As a result, β-phenyl-γ-butylolactone was obtained at a yield of 96%, and the lactone was composed mainly of the S isomer with the enatiomer excess percentage of 79% ee.

Example 34

Example 34 was effected in the same manner as in Example 20 except that the Co (III) (salen) complex (3.7 mg, 5.0 μmol) having the above formula (XI) (3.7 mg, 5.0 μmol) was used instead of the Co (III) (salen) complex (4.3 mg, 5.0 μmol) having the above formula (XII) (4.3 mg, 5.0 μmol). As a result, β-phenyl-γ-butylolactone was obtained at a yield of 82%, and the lactone was composed mainly of the S isomer with the enatiomer excess percentage of 75% ee.

Example 35

Example 33 was effected in the same manner as in Example 21 except that the Co (III) (salen) complex (3.7 mg, 5.0 μmol) having the above formula (XI) (3.7 mg, 5.0 μmol) was used instead of the Co (III) (salen) complex (4.3 mg, 5.0 μmol) having the above formula (XII) (4.3 mg, 5.0 μmol). As a result, β-phenyl-γ-butylolactone was obtained at a yield of 99%, and the lactone was composed mainly of the S isomer with the enatiomer excess percentage of 75% ee.

Example 36

Example 36 was effected in the same manner as in Example 22 except that the Co (III) (salen) complex (3.7 mg, 5.0 μmol) having the above formula (XI) (3.7 mg, 5.0 μmol) was used instead of the Co (III) (salen) complex (4.3 mg, 5.0 μmol) having the above formula (XII) (4.3 mg, 5.0 μmol). As a result, β-phenyl-γ-butylolactone was obtained at a yield of 89%, and the lactone was composed mainly of the S isomer with the enatiomer excess percentage of 69% ee.

It is seen from Examples 33 to 36 that the complexes corresponding to the precursors of the cationic cobalt(salen) complexes are effective for the asymmetric Baeyer-Villiger oxidation of the cyclic ketone compounds.

Example 37

Into 0.5 ml of ethanol was dissolved tricyclo[4,2,1,0³,⁹] nonane-2-one (13.6 mg, 0.1 mmol). Into this ethanol solution was added the Co (III) (salen) complex (3.7 mg, 5 μmol) having the above formula (XI). Into this solution was added 30% hydrogen peroxide aqueous solution (15 μl, hydrogen peroxide content 0.13 mmol), which was stirred at room temperature for 24 hours. After the completion of the reaction, the mixed liquid was concentrated, and the residue was chromatographed in a silica gel column with hexane/ethyl acetate (=8/2) as a developing solvent, thereby obtaining 2-oxatricyclo[5.2.1.0$^{4,10}$]decane-3-one (4.7 mg, yield 31%) having the above formula (VIII). The enantiomer excess percentage of the product was determined as follows.

Benzyl amine (110 ml, 1.0 mmol) was dissolved into dichloromethane (1.5 ml), and trimethyl aluminum (0.98 M hexane solution 1.0 ml, 1.0 mmol) was added into this solution at room temperature, followed by stirring for one hour. The resulting aluminum-amide solution (1.0 ml) was added into the above 2-oxatricyclo[5.2.1.0$^{4,10}$]decane-3-one (4.7 ml) at room temperature. After the mixture was stirred for 24 hours, the mixed liquid was quenched with 1M HCl aqueous solution and subjected to extraction with dichloromethane. The extract was dried over anhyrous MgSO$_4$, and concentrated. The residue was chromatographed on silica gel column using hexane/ethyl acetate (=8/2), thereby obtaining corresponding γ-hydroxybenzyl amide. Analysis of the enantiomeric excess percentage with Daicel Chiralcell OB-H and by a high speed liquid chromatography with hexane/isopropanol (=9/1) revealed that the product was composed mainly of 1R, 4S, 7S and 10 R isomers with the enantiomeric excess percentage of 36% ee. Results are shown in Table 4.

Example 38

Example 38 was effected in the same manner as in Example 37 except that the urea-hydrogen peroxide adduct (UHP) (12 mg, hydrogen peroxide content 0.13 mmol) was used instead of the 30% hydrogen peroxide aqueous solution (15 μl, hydrogen peroxide content 0.13 mmol). Results are shown in Table 4.

Example 39

Example 39 was effected in the same manner as in Example 38 except that acetonitrile (CH$_3$CN) (0.5 ml) was used instead of ethanol (EtOH) (0.5 ml). Results are shown in Table 4.

Example 40

Example 40 was effected in the same manner as in Example 38 except that diethyl ether (EtO$_2$) (0.5 ml) was used instead of ethanol (EtOH) (0.5 ml). Results are shown in Table 4.

Example 41

Example 41 was effected in the same manner as in Example 38 except that ethyl acetate (AcOEt) (0.5 ml) was used instead of ethanol (EtOH) (0.5 ml). Results are shown in Table 4.

Example 42

Example 42 was effected in the same manner as in Example 41 except that the stirring time (reaction time) was changed to 48 hours. Results are shown in Table 4.

Example 43

Example 43 was effected in the same manner as in Example 42 except that the Co (III) (salen) complex (4.1 mg, 5.0 μmol) having the above formula (XIV) was used instead of the Co (III) (salen) complex (3.7 mg, 5.0 μmol) having the above formula (XI).

Example 44

Example 44 was effected in the same manner as in Example 42 except that the Co (III) (salen) complex (5.0 mg, 5.0 μmol) having the above formula (XV) was used instead of the Co (III) (salen) complex (3.7 mg, 5.0 μmol) having the above formula (XI).

Example 45

Example 45 was effected in the same manner as in Example 42 except that the Co (III) (salen) complex (5.1 mg, 5.0 μmol) having the above formula (XVII) was used instead of the Co (III) (salen) complex (3.7 mg, 5.0 μmol) having the above formula (XI).

Example 46

Example 46 was effected in the same manner as in Example 42 except that the Co (III) (salen) complex (4.4 mg, 5.0 μmol) having the above formula (XVIII) was used instead of the Co (III) (salen) complex (3.7 mg, 5.0 μmol) having the above formula (XI).

TABLE 4

|  | catalyst | oxidant | solvent | time (h) | yield (%) | enantiomeric excess percentage (% ee) | configuration |
|---|---|---|---|---|---|---|---|
| Example 37 | formula (XI) | H$_2$O$_2$ | EtOH | 24 | 31 | 36 | 1R, 4S, 7S, 10R |
| Example 38 | formula (XI) | UHP | EtOH | 24 | 38 | 43 | 1R, 4S, 7S, 10R |
| Example 39 | formula (XI) | UHP | CH$_3$CN | 24 | 15 | 55 | 1R, 4S, 7S, 10R |
| Example 40 | formula (XI) | UHP | Et$_2$O | 24 | 15 | 56 | 1R, 4S, 7S, 10R |
| Example 41 | formula (XI) | UHP | AcOEt | 24 | 21 | 59 | 1R, 4S, 7S, 10R |
| Example 42 | formula (XI) | UHP | AcOEt | 48 | 42 | 60 | 1R, 4S, 7S, 10R |
| Example 43 | formula (XIV) | UHP | AcOEt | 48 | 36 | 76 | 1R, 4S, 7S, 10R |

TABLE 4-continued

|  | catalyst | oxidant | solvent | time (h) | yield (%) | enantiomeric excess percentage (% ee) | configuration |
|---|---|---|---|---|---|---|---|
| Example 44 | formula (XV) | UHP | AcOEt | 48 | 26 | 86 | 1R, 4S, 7S, 10R |
| Example 45 | formula (XVII) | UHP | AcOEt | 48 | 49 | 64 | 1R, 4S, 7S, 10R |
| Example 46 | formula (XVIII) | UHP | AcOEt | 48 | 92 | 98 | 1R, 4S, 7S, 10R |

The reaction formula corresponding to Examples 37-46 in Table 4 is shown below.

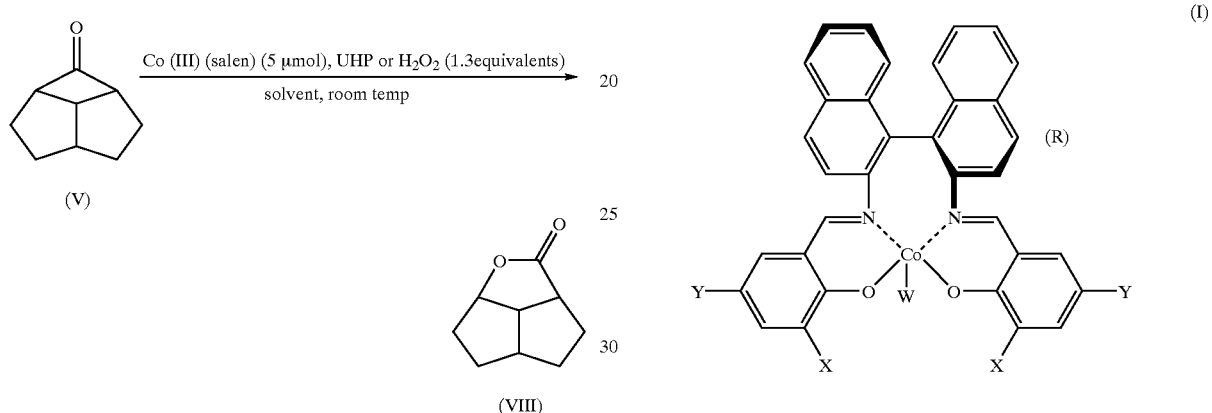

It is seen from Table 4 that the complexes according to the present invention are effective for the Baeyer-Villiger oxidation of the cyclic ketones having the above formula (V).

As mentioned above, the optically active lactone compounds can be produced by the producing method of the invention, and the lactone compounds having high optical purities of not less than 47% ee can be produced by appropriately selecting the reacting condition. Further, according to the present invention, inexpensive alcohols and ethers can be used as the solvent, while inexpensive hydrogen peroxide can be used as the oxidant. Therefore, the invention method has the economical advantage that the costs of the raw materials can be reduced. Thus, the optically active lactone compounds to be used for the synthesis of medicines and argochemicals can be produced at high optical purities.

What is claimed is:

1. A method for producing an optically active lactone compound by Baeyer-Villiger oxidation of a cyclic ketone compound with at least one kind of oxidants selected from the group consisting of hydrogen peroxide and urine-hydrogen peroxide adduct (UHP) using a cobalt(salen) complex having a cis-β structure expressed by the following formula (I) or (II) as a catalyst.

[Formula (I)]

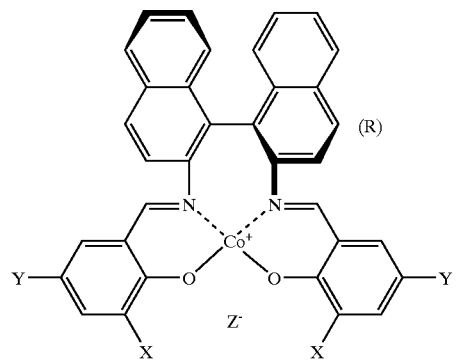

in which X and Y independently denote H, a t-butyl group or an electron-withdrawing substituting group and W is a halogen element.

Formula (II)

in which X and Y independently denote H, a t-butyl group or an electron-withdrawing substituting group and $Z^-$ is a monovalent anion.

2. The method set forth in claim 1, wherein X and Y in the cobalt(salen) complex of the formula (I) independently denote a t-butyl group, F, Cl, Br, I or a nitro group.

3. The method set forth in claim 2, wherein X and Y in the cobalt(salen) complex of the formula (I) denote a t-butyl group and a nitro group, respectively.

4. The method set forth in claims 3, wherein W in the cobalt(salen) complex of the formula (I) denotes iodine.

5. The method set forth in claim 1, wherein X and Y in the cobalt(salen) complex of the formula (II) independently denote F, Cl, Br or I.

6. The method set forth in claim 5, wherein X and Y in the cobalt(salen) complex of the formula (II) denote F.

7. The method set forth in claim 6, wherein $Z^-$ in the cobalt(salen) complex of the formula (II) denotes $SbF_6^-$.

8. The method set forth in claim 1, wherein the cyclic ketone compound is represented by any one of the following formulae (III), (IV) and (V).

Formula (III)

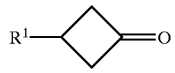

(III)

in which $R^1$ is a substituted or non-substituted C1–C20 alkyl group or a substituted or non-substituted C6–C15 aryl group.

Formula (IV)

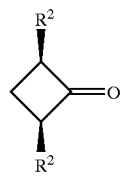

(IV)

in which $R^2$ is a substituted or non-substituted C1–C20 alkyl group or a substituted or non-substituted C6–C15 aryl group.

Formula (V)

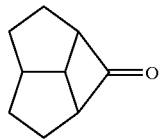

(V)

9. The method set forth in claim 8, wherein the cyclic ketone compound is represented by the formula (III).

10. The method set forth in claim 9, wherein the cyclic ketone compound is 3-phenylcyclobutanone, 3-(p-chlorophenyl)cyclobutanone, 3-(p-methoxy-phenyl)-cyclobutanone or 3-octyl cyclobutanone.

11. The method set forth in claim 8, wherein the cyclic ketone compound is represented by the formula (V).

12. The method set forth in claim 1, wherein the lactone compound is represented by any one of the following formulae (VI), (VII) and (VIII).

Formula (VI)

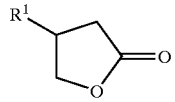

(VI)

in which $R^1$ is a substituted or non-substituted C1–C20 alkyl group or a substituted or non-substituted C6–C15 aryl group.

Formula (VII)

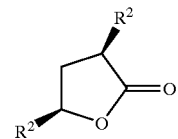

(VII)

in which $R^2$ is a substituted or non-substituted C1–C20 alkyl group or a substituted or non-substituted C6–C15 aryl group.

Formula (VIII)

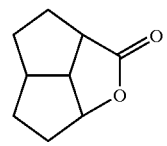

(VIII)

13. The method set forth in claim 12, wherein the lactone compound is represented by the formula (VI).

14. The method set forth in claim 13, wherein the lactone compound is β-phenyl-γ-butylolactone, β-(p-chlorophenyl)-γ-butylolactone, β-(p-methoxyphenyl)-γ-butylolactone or β-octyl-γ-butylolactone.

15. The method set forth in claim 12, wherein the lactone compound is represented by the formula (VIII).

16. The method set forth in claim 1, wherein the lactone compound has an optical purity of more than 47% ee.

17. The method set forth in claim 1, which uses at least one kind of polar solvents.

18. The method set forth in claim 17, wherein the polar solvent is any one selected from acetonitrile, ethyl acetate, diethyl ether, tetrahydrofuran (THF) and a C1–C3 alcohol.

19. The method set forth in claim 1, wherein the Baeyer-Villiger oxidation is effected in a temperature range of –20° C. to 0° C.

20. A cobalt(salen) complex having a cis-β structure represented by the following formula (I) or (II).

Formula (I)

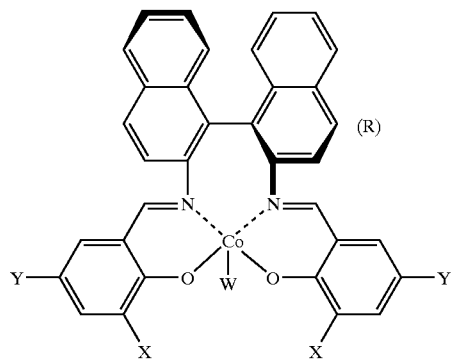

(I)

in which in which X and Y independently denote H, a t-butyl group or an electron-withdrawing substituting group and W is a halogen element.

Formula (II)

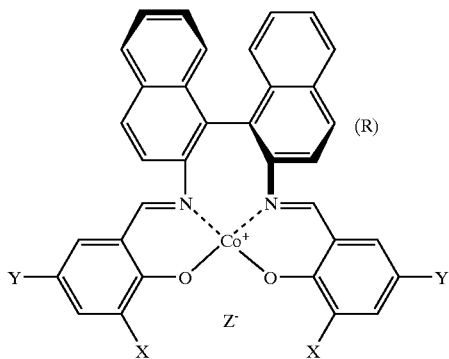

in which X and Y independently denote H, a t-butyl group or an electron-withdrawing substituting group and Z⁻ is a monovalent anion.

21. The method set forth in claim 20, wherein X and Y in the cobalt(salen) complex of the formula (I) independently denote a t-butyl group, F, Cl, Br, I or a nitro group.

22. The method set forth in claim 21, wherein X and Y in the cobalt(salen) complex of the formula (I) denote a t-butyl group and a nitro group, respectively.

23. The method set forth in claim 22, wherein W in the cobalt(salen) complex of the formula (I) denotes iodine.

24. The method set forth in claim 20, wherein X and Y in the cobalt(salen) complex of the formula (II) independently denote F, Cl, Br or I.

25. The method set forth in claim 24, wherein X and Y in the cobalt(salen) complex of the formula (II) denote F.

26. The method set forth in claim 25, wherein Z⁻ in the cobalt(salen) complex of the formula (II) denotes $SbF_6^-$.

27. The method set forth in claim 2, wherein W in the cobalt(salen) complex of the formula (I) denotes iodine.

28. The method set forth in claim 1, wherein W in the cobalt(salen) complex formula (I) denotes iodine.

29. The method set forth in claim 5, wherein Z in the cobalt(salen) complex formula (II) denotes $SbF_6^-$.

30. The method set forth in claim 1, wherein Z in the cobalt(salen) complex formula (II) denotes $SbF_6^-$.

31. The method set forth in claim 21, wherein W in the cobalt(salen) complex of the formula (I) denotes iodine.

32. The method set forth in claim 20, wherein W in the cobalt(salen) complex of the formula (I) denotes iodine.

33. The method set forth in claim 24, wherein Z in the cobalt(salen) complex of the formula (II) denotes $SbF_6^-$.

34. The method set forth in claim 20, wherein Z in the cobalt(salen) complex of the formula (II) denotes $SbF_6^-$.

* * * * *